US012788307B2

(12) United States Patent
Ramachandran et al.

(10) Patent No.: US 12,788,307 B2
(45) Date of Patent: Nov. 10, 2026

(54) NEUROMUSCULAR ASSESSMENT SYSTEM FOR DETECTING SYMPTOMS OF PARKINSON'S OR PRE-PARKINSON'S DISEASE BASED ON MOTOR UNIT SPIKE TRAINS FROM ELECTROMYOGRAPHY SIGNALS

(71) Applicant: Analog Devices, Inc., Wilmington, MA (US)

(72) Inventors: Supriya Balaji Ramachandran, Fremont, CA (US); Joann Close, Los Altos, CA (US); Eileen Marie Staskunas, San Diego, CA (US); Milos Todorovic, Northborough, MA (US); Rebecca A. Williams, Vancouver, WA (US)

(73) Assignee: Analog Devices, Inc., Wilmington, MA (US)

( * ) Notice: Subject to any disclaimer, the term of this patent is extended or adjusted under 35 U.S.C. 154(b) by 558 days.

(21) Appl. No.: 18/199,180

(22) Filed: May 18, 2023

(65) Prior Publication Data

US 2026/0076612 A1 Mar. 19, 2026

(51) Int. Cl.
*A61B 5/00* (2006.01)
*A61B 5/0205* (2006.01)
(Continued)

(52) U.S. Cl.
CPC .......... *A61B 5/4082* (2013.01); *A61B 5/0205* (2013.01); *A61B 5/313* (2021.01); (Continued)

(58) Field of Classification Search
CPC ..... A61B 5/4082; A61B 5/0205; A61B 5/313; A61B 5/397; A61B 5/02416; A61B 2562/0219
See application file for complete search history.

(56) References Cited

U.S. PATENT DOCUMENTS 9,302,046 B1 4/2016 Giuffrida et al.
9,592,379 B2 3/2017 Heruth et al.
(Continued)

FOREIGN PATENT DOCUMENTS

WO WO-2023209150 A1 * 11/2023 ......... A61N 1/36062

OTHER PUBLICATIONS

Hug et al (Correlation networks of spinal motor neurons that innervate lower limb muscles during a multi-joint isometric task, J Physiol 601.15 (2023) pp. 3201-3219, published online Jun. 30, 2022).*

(Continued)

*Primary Examiner* — Serkan Akar
(74) *Attorney, Agent, or Firm* — ArentFox Schiff LLP

(57) ABSTRACT

A neuromuscular assessment system and method of operation can include: affixing a first electrode array to an agonist muscle configured to detect a first Electromyography (EMG) signal; affixing a second electrode array to an antagonist muscle configured to detect a second EMG signal, the agonist muscle and the antagonist muscle forming an agonist/antagonist muscle pair; decomposing the first EMG signal into a first motor unit spike train; decomposing the second EMG signal into a second motor unit spike train; correlating the first motor unit spike train and the second motor unit spike train to generate correlated signals; determining synchronicity and periodicity within the correlated signals; and generating a tremor fraction, the tremor fraction being a percentage of the correlated signals determined to have both the synchronicity and the periodicity.

21 Claims, 13 Drawing Sheets

(51) Int. Cl.
*A61B 5/024* (2006.01)
*A61B 5/313* (2021.01)
*A61B 5/397* (2021.01)

(52) U.S. Cl.
CPC .......... *A61B 5/397* (2021.01); *A61B 5/02416* (2013.01); *A61B 2562/0219* (2013.01)

(56) References Cited

U.S. PATENT DOCUMENTS

| | | | | |
|---|---|---|---|---|
| 2013/0123666 A1* | 5/2013 | Giuffrida | A61N 1/36067 | |
| | | | 600/595 | |
| 2019/0001129 A1* | 1/2019 | Rosenbluth | A61N 1/36014 | |
| 2021/0106281 A1* | 4/2021 | Tran | A61B 5/486 | |

OTHER PUBLICATIONS

Dai et al (Independent component analysis-based algorithms for high-density electromyogram decomposition: Systematic evaluation through simulation, Computers in Biology and Medicine, vol. 109, Jun. 2019, pp. 171-181).*

Germer et al (Surface EMG cross talk quantified at the motor unit population level for muscles of the hand, thigh, and calf. J Appl Physiol 131: 808-820, 2021).*

Crawford et al (Tremor: Sorting Through the Differential Diagnosis, American Family Physician, Feb. 1, 2018, vol. 97, No. 3).*

P. Povalej Bržan et al., "New Perspectives for Computer-Aided Discrimination of Parkinson's Disease and Essential Tremor", vol. 2017, Oct. 19, 2017, pp. 1-17 https://onlinelibrary.wiley.com/doi/epdf/10.1155/2017/4327175.

Juan A. Gallego et al., "The Phase Difference Between Neural Drives to Antagonist Muscles in Essential Tremor Is Associated with the Relative Strength of Supraspinal and Afferent Input", The Journal of Neuroscience, Jun. 10, 2015, vol. 35, No. 23, pp. 8925-8937 https://www.jneurosci.org/content/jneuro/35/23/8925.full.pdf.

Xinkai Wang et al., "The Effects of Deep Brain Stimulation on Motor Unit Activities in Parkinson's Disease based on High-Density Surface EMG Analysis", 2022 44th Annual International Conference of the IEEE Engineering in Medicine & Biology Society (EMBC), IEEE, Jul. 11, 2022, pp. 682-685.

Noah Rubin et al., "Common Neural Input within and across Lower Limb Muscles: A Preliminary Study", 2021 43rd Annual International Conference of the IEEE Engineering in Medicine & Biology Society (EMBC), IEEE, Oct. 31, 2021, pp. 6683-6686.

Ashkan Hosseinzadeh Namin, Karl Leboeuf, Huapeng Wu, and Majid Ahmadi, "Artificial Neural Networks Activation Function HDL Coder", Department of Electrical and Computer Engineering, University of Windsor, Windsor, Ontario N9B 3P4, Canada, Jul. 2009 https://www.researchgate.net/figure/The-Hyperbolic-Tangent-and-The-Sigmoid-Activation-Functions_fig1_224570545.

Ales Holobar and Damjan Zazula, "Gradient Convolution Kernel Compensation Applied to Surface Electromyograms", (LISIN, Politecnico di Torino, Torino, Italy) and (Faculty of Electrical Engineering and Computer Science, University of Maribor, Maribor, Slovenia), Sep. 2007 https://dl.acm.org/doi/10.5555/1776684.1776766.

Bruno Mambrito and Carlo J. De Luca, "A Technique for the Detection, Decomposition and Analysis of the EMG Signal", Electroencephalography and clinical Neurophysiology, Feb. 16, 1984, Elsevier Scientific Publishers reland, Ltd.

* cited by examiner

NEUROMUSCULAR ASSESSMENT SYSTEM FOR DETECTING SYMPTOMS OF PARKINSON'S OR PRE-PARKINSON'S DISEASE BASED ON MOTOR UNIT SPIKE TRAINS FROM ELECTROMYOGRAPHY SIGNALS

TECHNICAL FIELD

This disclosure relates to health assessment systems, more particularly to neuromuscular assessment systems with Electromyography (EMG) arrays configured to detect neural drive limbic-motor symptoms of Parkinson's and pre-Parkinson's neurodegeneration.

BACKGROUND

Parkinson's disease is a neurological movement disorder caused by loss of dopamine secreting neurons in the midbrain. Motor symptoms of Parkinson's disease can include resting tremor, slowness of movement (Bradykinesia), stiff muscles, unsteady walk (Gait anomalies), balance problems, and coordination problems.

Early diagnosis is important. By the time the motor symptoms are diagnosed, 70% of all dopamine neurons may have been lost, at which time treatments become largely ineffective. Medical costs increase with disease progression, sometimes expensive institutional care is required in deteriorated conditions.

Illustratively, for example, treatments such as levodopa and carbidopa are more effective when administered early in the disease. Non-pharmacologic treatments, such as increased exercise, are also easier to perform in the early stages of Parkinson's disease and may help slow down disease progression.

Nearly one million people in the U.S. are living with Parkinson's disease while seven million people worldwide live with Parkinson's disease. The number of people living with Parkinson's disease in the U.S. is expected to rise to 1.2 million by 2030. In 2017, the direct medical costs associated with Parkinson's disease was $25.4 billion, which is expected to grow with time.

Many previous developments in monitoring technology for Parkinson's disease rely on monitoring of conspicuous Parkinson's motor symptoms that correspond to the visible and later stage of the disease. This is primarily due to previous developments in monitoring technology employing a limited number of EMG sensors individually placed on a patient's skin.

This previous monitoring technology can distinguish visually observable symptoms but fails to provide insight into the pre-motor neurodegeneration that is characteristic of pre-Parkinson's conditions. Illustratively, previous monitoring technologies employ a limited number of EMG sensors placed individually by a health care professional on a patient's skin to monitor muscle drive.

Because these sensors are limited in number and not formed in any sort of array or fixed position with regard to each other; the detection, triangulation, and measurement of the pre-motor neural drive for individual motor units is impossible to determine. Previous monitoring technologies therefore implemented technical processes which failed to account for the pre-motor, neural origins, of Parkinson's symptoms leading to an inability to identify pre-Parkinson's conditions and provides only measurements of late stage symptoms.

Utilizing this previous monitoring technology, evidence suggests that nearly half (47%) of Parkinson's disease diagnoses are incorrect when performed in the primary care setting. Specialists whose expertise is not specific movement disorders have an error rate of approximately 25% while movement disorder specialists are mistaken in only 6% to 8% of cases.

Even when properly diagnosed by healthcare professionals utilizing the previous monitoring technology, up to 70% of neurons are possibly lost by the time a movement disorder specialist identifies Parkinson's disease since the disease is detectable with the previous monitoring technology based on EMG signals corresponding to visible and late stage Parkinson's disease symptoms.

Solutions have been long sought but prior developments have not taught or suggested any complete solutions, and solutions to these problems have long eluded those skilled in the art. Thus, there remains a considerable need for devices and methods that can detect and identify the neural origins for individual motor units for generating, monitoring, and tracking pre-Parkinson's disease information, which can enable early diagnoses.

SUMMARY

A neuromuscular assessment system and methods, for the generating, monitoring, and tracking of pre-Parkinson's disease information within pre-motor neural origins is disclosed. Rather than relying on late-stage, conspicuous motor symptoms the neuromuscular assessment system is set forth with technical features which enable the use of pre-motor neural origins, which provide early pre-motor signatures of neurodegeneration.

The neuromuscular assessment system and methods of operation can include: affixing a first electrode array to an agonist muscle configured to detect a first Electromyography (EMG) signal; affixing a second electrode array to an antagonist muscle configured to detect a second EMG signal, the agonist muscle and the antagonist muscle forming an agonist/antagonist muscle pair; decomposing the first EMG signal into a first motor unit spike train; decomposing the second EMG signal into a second motor unit spike train; correlating the first motor unit spike train and the second motor unit spike train to generate correlated signals; determining synchronicity and periodicity within the correlated signals; and generating a tremor fraction, the tremor fraction being a percentage of the correlated signals determined to have both the synchronicity and the periodicity.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The neuromuscular assessment system is illustrated in the figures of the accompanying drawings which are meant to be exemplary and not limiting, in which like reference numerals are intended to refer to like components, and in which.

DETAILED DESCRIPTION

Figure 1:
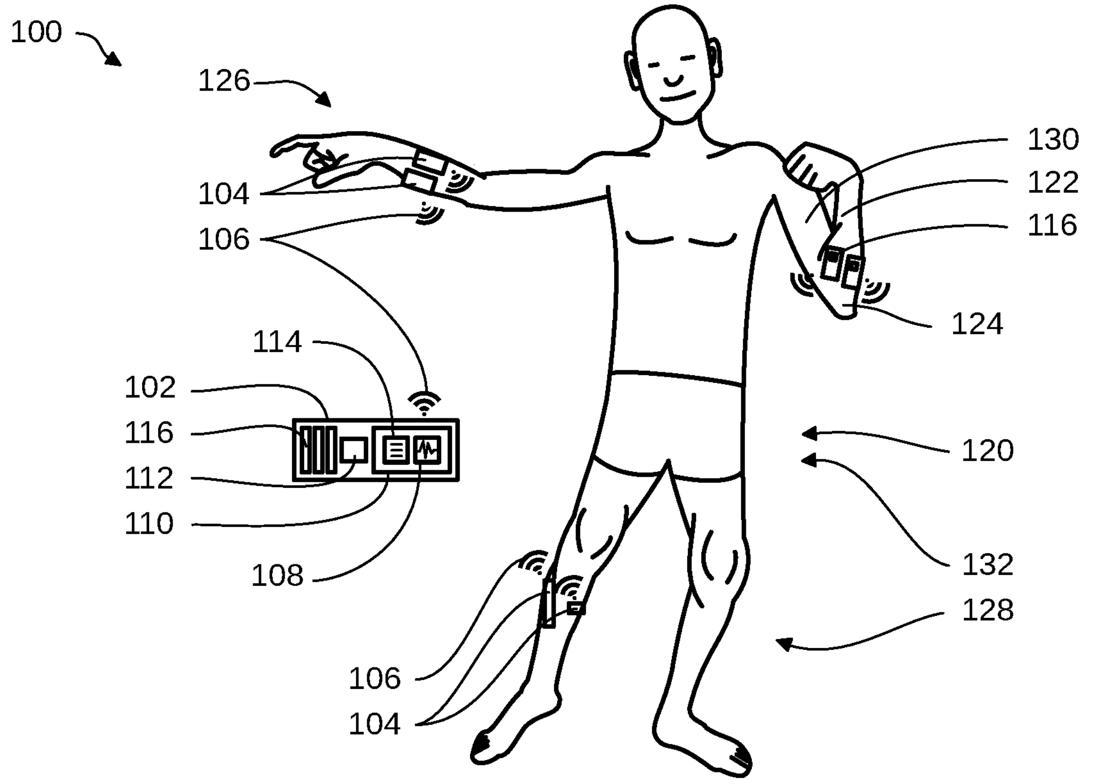
FIG. 1 is a side view of the neuromuscular assessment system.

In the following description, reference is made to the accompanying drawings that form a part hereof, and in which are shown by way of illustration, embodiments in which the neuromuscular assessment system may be practiced. It is to be understood that other embodiments may be utilized and structural changes may be made without departing from the scope of the neuromuscular assessment system.

When features, aspects, or embodiments of the neuromuscular assessment system are described in terms of steps of a process, an operation, a control flow, or a flow chart, it is to be understood that the steps can be combined, performed in a different order, deleted, or include additional steps without departing from the neuromuscular assessment system as described herein.

The neuromuscular assessment system is described in sufficient detail to enable those skilled in the art to make and use the neuromuscular assessment system and provide numerous specific details to give a thorough understanding of the neuromuscular assessment system; however, it will be apparent that the neuromuscular assessment system may be practiced without these specific details.

In order to avoid obscuring the neuromuscular assessment system, some well-known assessment system configurations, algorithms, and descriptions are not disclosed in detail. Likewise, the drawings showing embodiments of the assessment system are semi-diagrammatic and not to scale and, particularly, some of the dimensions are for the clarity of presentation and are shown greatly exaggerated in the drawing FIGs.

As used herein, the term "couple" as in "coupled" or "coupling" is to be understood herein as a physical connection between elements whether direct or indirect. As used herein "correlated signals" means auto-correlated signals, cross-correlated signals, or a combination thereof.

Referring now to FIG. 1, therein is shown a side view of the neuromuscular assessment system 100. The neuromuscular assessment system 100 can include a components box 102 coupled to combination sensors 104.

It is contemplated that the components box 102 and the combination sensors 104 can be formed as an integral unit or could be communicatively coupled through a cable or utilizing wireless transmission. The combination sensors 104 are described in greater detail below with regard to FIG. 2, FIG. 4, and FIG. 5. As depicted, each of the combination sensors 104 are communicatively coupled, through a wireless transmission 106, to the components box 102.

The wireless transmission 106 can be accomplished by transponders built into the combination sensors 104 communicating with a transponder built into the components box 102. The wireless transmission 106 can communicate a combination sensor output signal 108 to the components box 102. It is contemplated that the combination sensor output signal 108 can be a digital representation of multiple sensor signals; such as those disclosed and described with regard to FIG. 2 and FIG. 8A-FIG. 8D, for example. When implemented with a communications cable between the combination sensors 104 and the components box 102, the combination sensor output signal 108 could include an I'C signal or an SPI interface signal.

The components box 102 can include a non-transitory computer readable medium 110, in useful association with a processor 112 for storing the combination sensor output signal 108 and storing instructions 114 for the operation and control of the neuromuscular assessment system 100. The processor 112 can be a processor contained within the components box 102 but is also contemplated to include a distributed processing network.

The components box 102 and the combination sensors 104 can further include power sources 116, such as a battery or an adaption for a public electricity outlet. In one contemplated embodiment, the power source 116 in the components box 102 can be used to provide power to the combination sensors 104 when coupled with a communication cable.

The combination sensors 104 can be paired up and attached to an agonist/antagonist muscle pair of a patient 120. Illustratively, for example, one pair of the combination sensors 104 are shown attached to lower arms 122 of the patient 120. Particularly, two of the combination sensors 104 are attached to a left arm 124 and two of the combination sensors 104 are attached to a right arm 126. The attachment of the combination sensors 104 to the right arm 126 of the patient 120 is depicted and described in greater detail with regard to FIG. 4.

For descriptive clarity, the combination sensors 104 are described as being affixed to the lower arms 122 of the patient 120 above the agonist/antagonist muscle pair of the Extensor Carpi Radialis (ECR) and the Flexor Carpi Radialis (FCR). The neuromuscular assessment system 100 can therefore monitor the left ECR, the right ECR, the left FCR, and the right FCR with the combination sensors 104.

Figure 5:
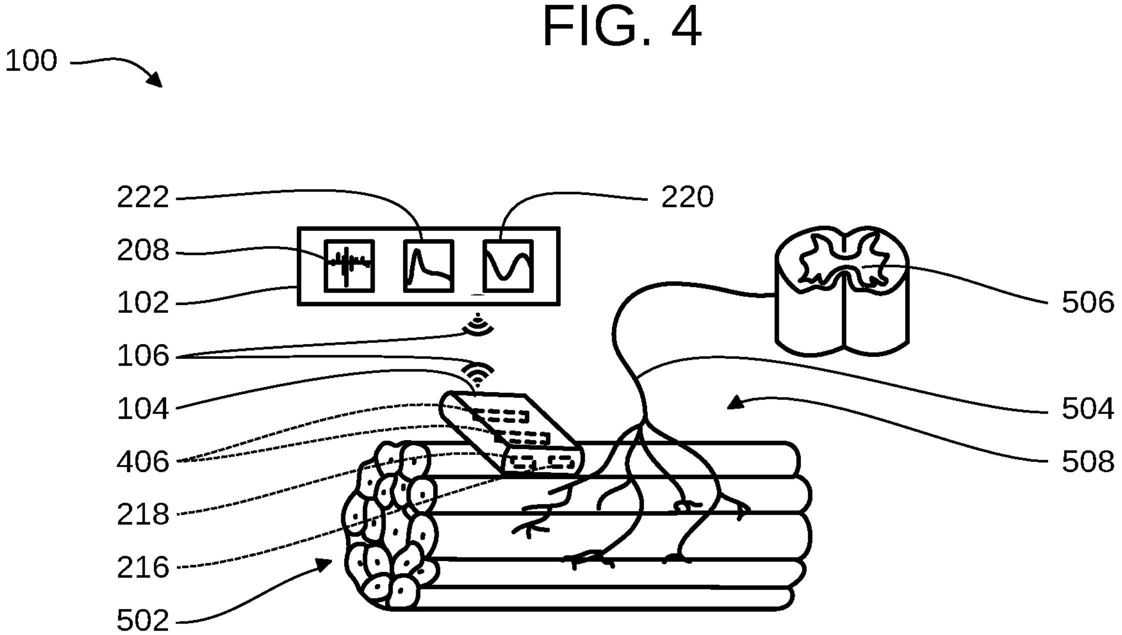
FIG. 5 is an isometric view of the neuromuscular assessment system of FIG. 1.

Further, one pair of the combination sensors 104 are shown attached to a lower leg 128 of the patient 120, which is depicted and described in greater detail with regard to FIG. 5. For descriptive clarity, the combination sensors 104 are depicted as placed on the Gastrocnemius and on the Tibialis anterior muscle.

It is contemplated that the combination sensors 104 could also be attached to other agonist/antagonist muscle pairs on upper arms 130, upper legs 132, hands, or feet of the patient 120. It is also contemplated that the agonist/antagonist muscle pair could be other muscle combinations within the lower arm 122 or lower leg 128 than depicted in FIG. 4 or FIG. 14, respectively.

Figure 2:
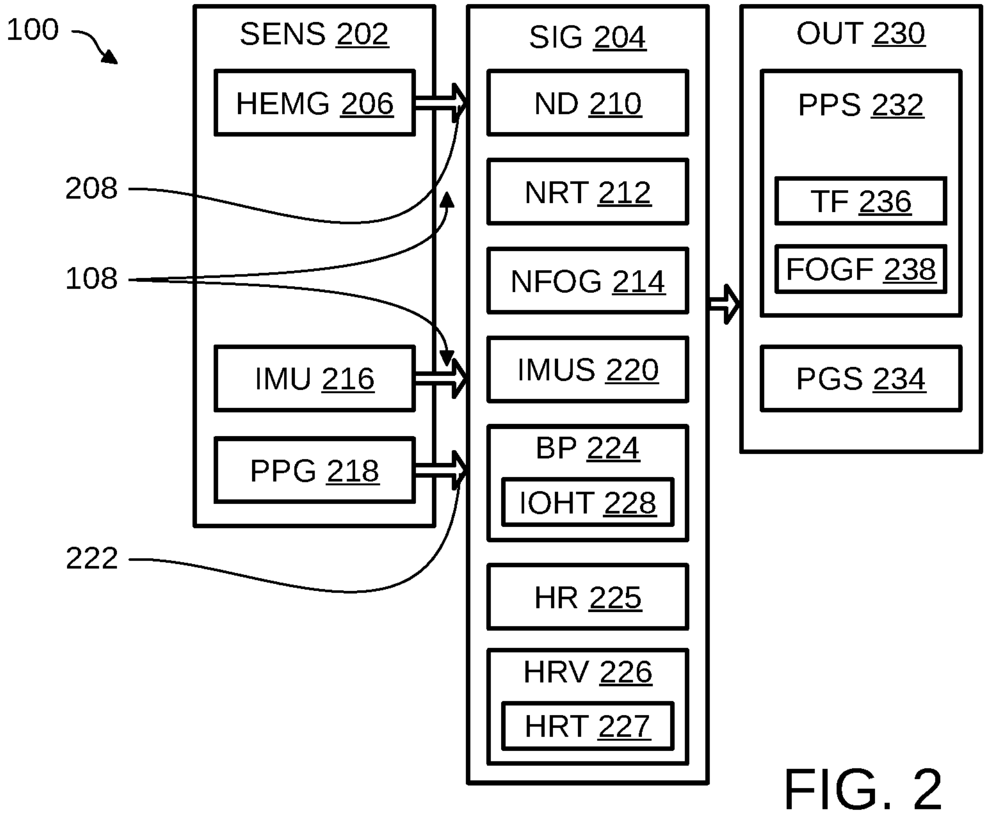
FIG. 2 is a block diagram of the neuromuscular assessment system of FIG. 1.

Referring now to FIG. 2, therein is shown a block diagram of the neuromuscular assessment system 100 of FIG. 1. The neuromuscular assessment system 100 is shown having a sensors block 202 representing the sensors within the combination sensor 104 of FIG. 1 and providing the combination sensor output signal 108 to a signals block 204. Illustratively, the sensors block 202 can include a high density-surface EMG (HD-sEMG 206). The HD-sEMG 206 can provide an HD-sEMG signal 208.

Figure 4:
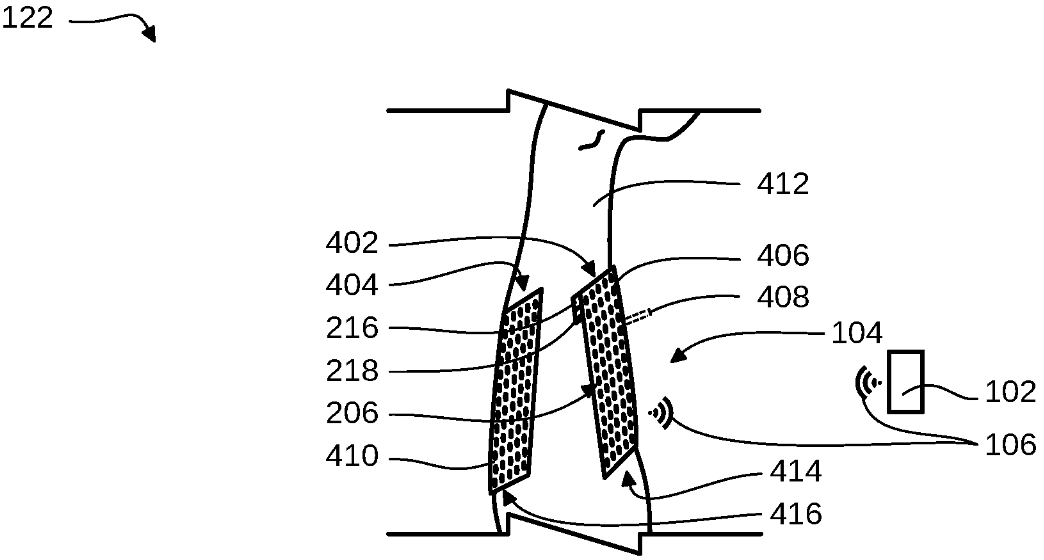
FIG. 4 is a side view of the lower arm of FIG. 1.
Figure 9A:
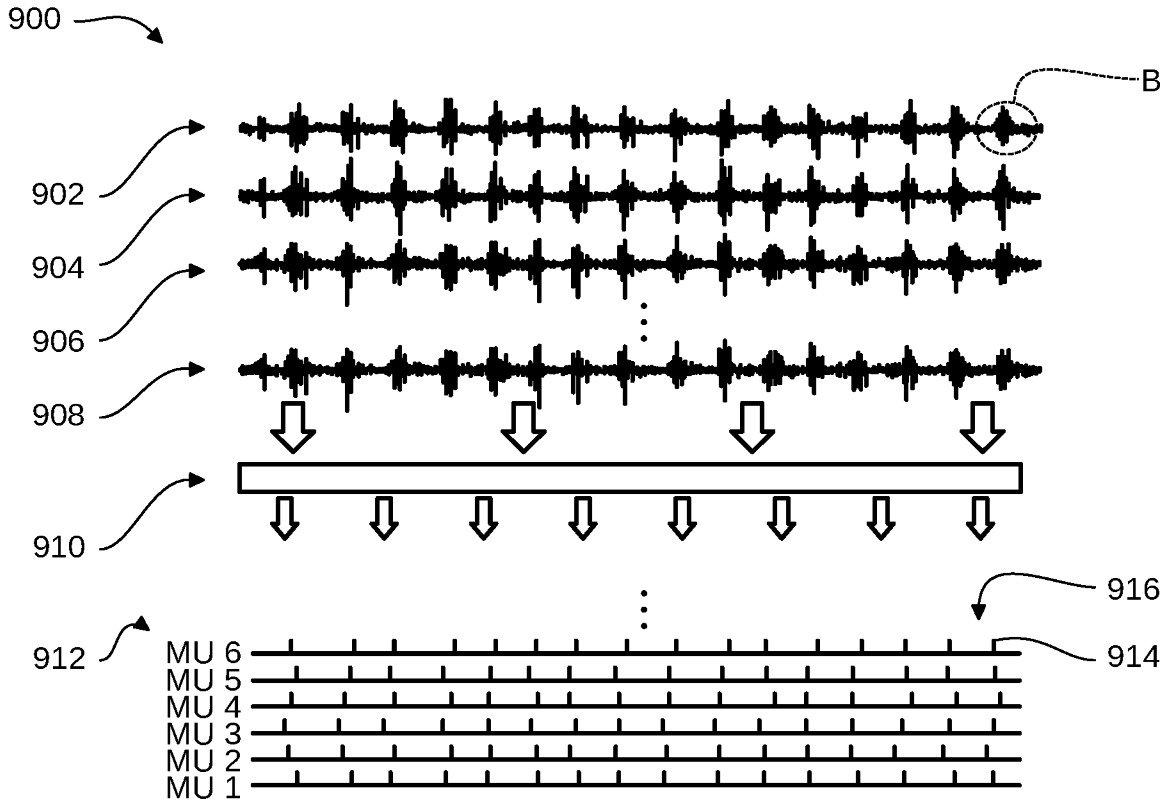
FIG. 9A is a graphical depiction of a decomposition process for the calculate neural drive step of FIG. 3A.

As shown in greater detail with regard to FIG. 4 and FIG. 9A, the HD-sEMG 206 can provide the multiple EMG channels of FIG. 9A with each of the EMG signal channels generated by one of the electrodes 406 of FIG. 4 configured within an array on the skin of the patient 120 of FIG. 1. As used herein an array of the electrodes 406 means a 2×1 or 1×2 array at a minimum, and is contemplated to include arrays of tens or hundreds of electrodes 406.

When the electrodes or electrode arrays are set forth as attached or affixed to a muscle, it is to be understood that the electrode or electrode array is attached or affixed indirectly to the muscle through the skin. The multiple EMG channels contained within the HD-sEMG signal 208 can be analyzed within the processor 112 of FIG. 1 and provide a neural drive signal 210.

The neural drive signal 210 can be a spatial triangulation of muscle activity and activation over time, such as the motor unit spike trains 912 depicted and described with regard to FIG. 9A. The neural drive signal 210 can be further processed, as described below with regard to FIG. 10 and FIG. 11A-FIG. 11L, to derive additional signals which are useful in generating and identifying pre-Parkinson's neurodegeneration information, which can enable early diagnoses.

Parkinson's and pre-Parkinson's neurodegeneration information can be generated by at least two physical conditions including resting tremor and freezing of gait. Resting tremor is a muscular tremor of about 4 Hz to 6 Hz and is the basis for the description of FIG. 3A-FIG. 11L.

Freezing of gait is an abnormal gait including temporary pauses of motion during a step and is the basis for the description of FIG. 12-FIG. 16B. As such, the neural drive signal 210 can be evaluated to provide a neural origin of resting tremor signal 212 and a neural origin of freeze of gait signal 214.

Illustratively, the neural origin of resting tremor signal 212 can be computed and determined from the neural drive signal 210 as described with regard to FIG. 8A-FIG. 11L. Furthermore, the neural origin of freeze of gait signal 214 can be computed and determined from the neural drive signal 210 as described with regard to FIG. 15A-FIG. 16B.

As used herein, the neural drive signal 210, the resting tremor signal 212, and the freeze of gait signal 214 are to be understood to be pre-Parkinson's disease information. The sensors block 202 can include other sensors than the HD-sEMG 206, such as an inertial measurement unit (IMU 216) and a PPG sensor 218. The IMU 216 can provide an IMU signal 220.

The IMU signal 220 can include magnetic readings, accelerometer readings, and gyroscope readings. The IMU signal 220, and particularly the accelerometer readings, can be used by the signals block 204 with little modification, as the acceleration of the combination sensor 104 is useful in the determination of both freeze of gait and resting tremor.

However, it has been discovered that the neural drive signal 210, providing the neural origin of freeze of gait signal 214 and the neural origin of resting tremor signal 212, is useful in generating and identifying pre-Parkinson's neurodegeneration information before the patient 120 exhibits even visible tremors or gait anomalies. Furthermore, it has been discovered that the neural drive signal 210 is sensitive enough to even generate pre-Parkinson's neurodegeneration information before tremors or gait anomalies appear in the acceleration readings of the IMU signal 220.

The incredible sensitivity and discrimination afforded by the neural drive signal 210 arises from the spatial triangulation of muscle drive activity depicted as the motor unit spike trains 912, and which rest on the HD-sEMG signal 208 being detectable by the combination sensor 104 and analyzed within the signals block 204 even when other physical traits, including tremors and gait anomalies, are not expressed by the patient 120 at a detectable level using the IMU 216 or the PPG sensor 218.

The PPG sensor 218 can provide a PPG signal 222. The PPG sensor 218 can produce a waveform based on variations in the attenuation that light energy passing through tissue of the patient 120. As described with regard to FIG. 8C, analysis of the PPG signal 222 within the signals block 204 can provide an indication of blood pressure 224 with an estimation of a systole pulse wave and diastole pulse wave. Further, a time interval between systole pulses can be determined, from which heart rate 225 and heart rate variability 226 can be derived.

While the heart rate variability 226 is not specific to Parkinson's it is correlated with Parkinson's and a heart rate variability threshold 227 is provided to determine if a Parkinson's level of heart rate variability is present. Similarly, initial orthostatic hypotension (IOH), which occurs when the blood pressure 224 drops during the initial thirty seconds after standing is correlated with Parkinson's disease.

When for example, the systole pulse wave 822 of FIG. 8 detects a drop of the blood pressure 224 below an IOH threshold 228 within thirty seconds of standing, IOH is present in the patient 120. As used herein, the IMU signal 220, blood pressure 224, heart rate 225, and heart rate variability 226 are to be understood as pre-Parkinson's disease information. Collectively, the neural drive signal 210, the neural origin of resting tremor signal 212, the neural origin of freeze of gait signal 214, the IMU signal 220, the blood pressure 224, the heart rate 225, and the heart rate variability 226 are herein to be considered neuromuscular signals.

An analysis of the combination sensor output signal 108 within the signals block 204, and executed on the processor 112, can be provided to an outcomes block 230. The outcomes block 230 can provide and display a Parkinson's propensity score 232 and a Parkinson's progression score 234.

The Parkinson's propensity score 232 and the Parkinson's progression score 234 can be displayed visually with a display or print out, through an audio device like a speaker, or through a tactile or haptic device. The Parkinson's propensity score 232 can be a tremor fraction 236 calculated as described with regard to FIG. 3A and a freeze of gait fraction 238 as described with regard to FIG. 12 or the Parkinson's propensity score 232 can be an average between the tremor fraction 236 and the freeze of gait fraction 238.

The tremor fraction 236 and the freeze of gait fraction 238 can be tracked over time and the change in both fractions can be provided to the patient 120 as the Parkinson's progression score 234. As used herein the Parkinson's propensity score 232, the Parkinson's progression score 234, the tremor fraction 236, and the freeze of gait fraction 238 are to be understood as pre-Parkinson's disease information.

Figure 3A:
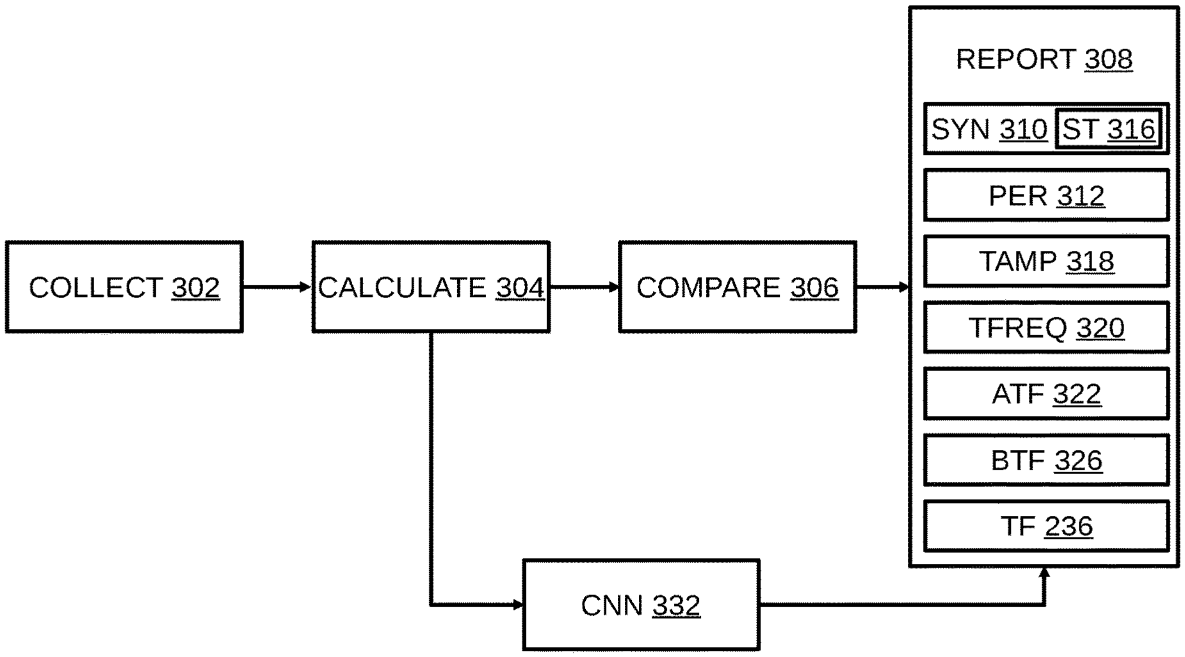
FIG. 3A is a control flow for computing resting tremor information for the neuromuscular assessment system of FIG. 1.

Referring now to FIG. 3A, therein is shown a control flow for computing resting tremor information for the neuromuscular assessment system 100 of FIG. 1. Illustratively, the control flow can include computing the tremor fractions 236 of FIG. 2. Computing the resting tremor information can be understood as generating pre-Parkinson's disease information. The neuromuscular assessment system 100 can begin to calculate the resting tremor information with a collection step 302.

The collection step 302 can include placing the HD-sEMG 206 of FIG. 2 on agonist/antagonist muscle pairs from two limbs, as described with regard to FIG. 1. For monitoring resting tremor, the FCR and ECR of the lower arm works well.

Resting tremor is a symptom of Parkinson's. Resting tremors are low frequency component of neural drive that are bi-laterally asymmetric and alternate contraction between agonist and antagonist muscles. Resting tremors can provide relatively sinusoidal displacement readings from the IMU 216 of FIG. 2. While resting tremors are periodic and synchronous between agonist/antagonist muscle pairs, voluntary contractions are asynchronous.

Previous developments failed at determining resting tremor prior to the tremors being observable by physical movement because the neural drive was not evaluated at the motor unit spike train 912 level of FIG. 9A or utilizing the correlation methods of FIG. 11A through FIG. 11L. This led to an inability to identify and discriminate resting tremor until after many early treatments are more difficult, expensive, or not viable.

Figure 8A:
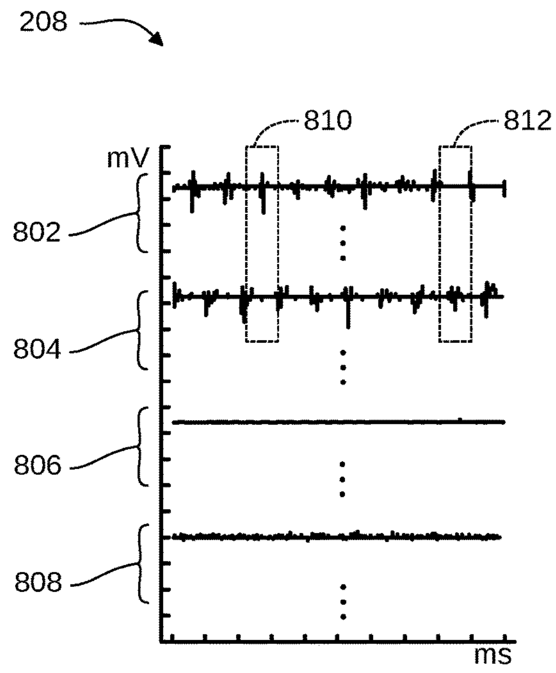
FIG. 8A is a graphical depiction of the HD-sEMG signal of the combination sensor of FIG. 1.

The collection step 302 can include the collection of the HD-sEMG signal 208 of FIG. 2 and further shown, for example in FIG. 8A. The HD-sEMG signals 208 can be collected or stored in the non-transitory computer readable medium 110 of FIG. 1 while the collection step 302 runs continuously.

It has been discovered that the HD-sEMG data provides richer information than traditional sEMG by providing a spatial dimension to EMG signals allowing the spatial triangulation of muscle activity and activation over time. This can be calculated as the neural drive signal 210 of FIG. 2 in a calculate neural drive step 304.

The neural drive signal 210 can be the motor unit spike trains 912. That is, the calculate neural drive step 304 can retrieve the HD-sEMG signal 208 from the HD-sEMG 206 and calculate the motor unit spike trains 912.

The operation of the calculate neural drive step 304 is described in greater detail with regard to FIG. 9A and involves the decomposition of the HD-sEMG signals 208 into individual Motor Unit Action Potentials (MUAPs 920) of FIG. 9A, which are abstracted to preserve only the spike times of the MUAPs 920 for each motor unit 508 of FIG. 5 into the motor unit spike trains 912. Once the motor unit spike trains 912 are calculated, the motor unit spike trains 912 can be summed to calculate and determine the cumulative spike train (CST 1002) of FIG. 10.

The CSTs 1002 can be calculated for each of the combination sensors 104 of FIG. 1. Continuing with the example from FIG. 1 for the left and right lower arms 122, the calculate neural drive step 304 can calculate a CST for each of the left ECR, the right ECR, the left FCR, and the right FCR.

The calculate neural drive step 304 can apply a low pass filter for frequencies above 20 hertz, for example. The low pass filtering of the calculate neural drive step 304 can be used to target the resting tremor which is a low frequency occurrence in the range of 4-6 hertz.

Once the CSTs 1002 are determined in the calculate neural drive step 304, the neuromuscular assessment system 100 can execute a CST comparison step 306. The CST comparison step 306 can calculate the correlated signals for the CSTs 1002.

Figure 11A:
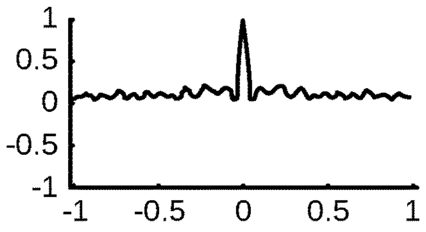
FIG. 11A is a graphical depiction of a CST auto-correlation for the left extensor carpi radialis (ECR) of FIG. 8A.
Figure 11B:
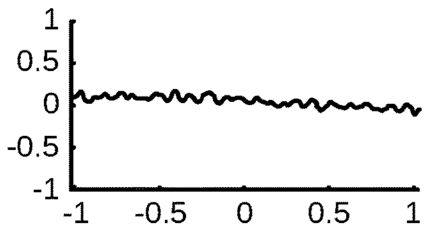
FIG. 11B is a graphical depiction of a CST cross-correlation between the left ECR of FIG. 8A and the left flexor carpi radialis (FCR) of FIG. 8A.
Figure 11C:
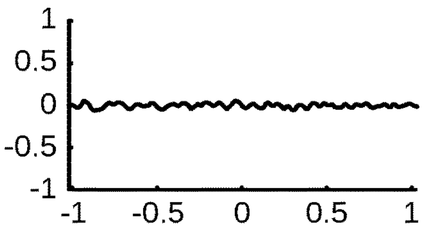
FIG. 11C is a graphical depiction of a CST cross-correlation between the left ECR of FIG. 8A and the right ECR of FIG. 8A.
Figure 11D:
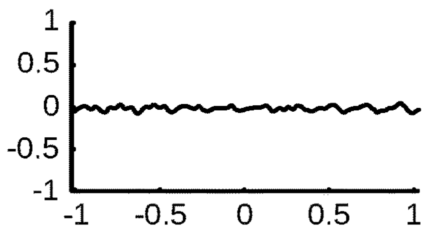
FIG. 11D is a graphical depiction of a CST cross-correlation between the left ECR of FIG. 8A and the right FCR of FIG. 8A.
Figure 11E:
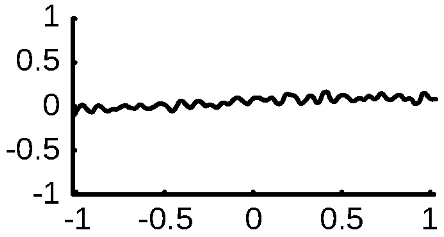
FIG. 11E is a graphical depiction of a CST cross-correlation between the left FCR of FIG. 8A and the left ECR of FIG. 8A.
Figure 11F:
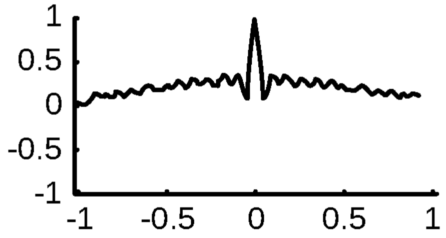
FIG. 11F is a graphical depiction of an CST auto-correlation for the left FCR of FIG. 8A.
Figure 11G:
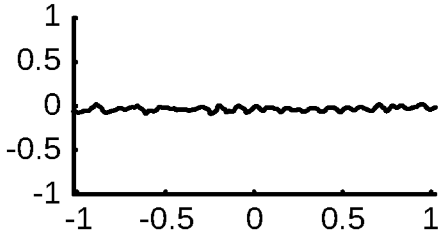
FIG. 11G is a graphical depiction of a CST cross-correlation between the left FCR of FIG. 8A and the right ECR of FIG. 8A.
Figure 11H:
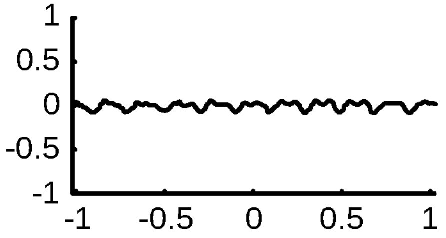
FIG. 11H is a graphical depiction of a CST cross-correlation between the left FCR of FIG. 8A and the right FCR of FIG. 8A.
Figure 11I:
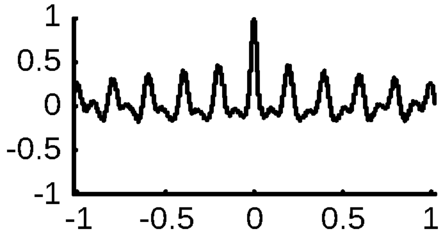
FIG. 11I is a graphical depiction of a CST auto-correlation for the right ECR of FIG. 8A.
Figure 11J:
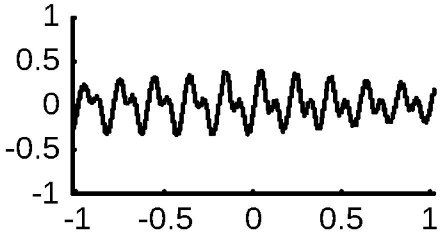
FIG. 11J is a graphical depiction of a CST cross-correlation between the right ECR of FIG. 8A and the right FCR of FIG. 8A.
Figure 11K:
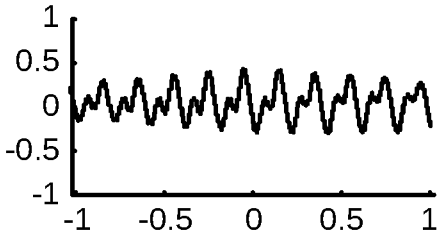
FIG. 11K is a graphical depiction of a CST cross-correlation between the right FCR of FIG. 8A and the right ECR of FIG. 8A.
Figure 11L:
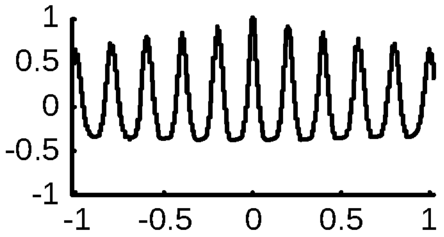
FIG. 11L is a graphical depiction of a CST auto-correlation for the right FCR of FIG. 8A.

Illustratively, auto-correlations can be calculated for the CST 1002 of the left ECR depicted in FIG. 11A, the CST 1002 of the right ECR depicted in FIG. 11I, the CST 1002 of the left FCR depicted in FIG. 11F, and the CST 1002 of the right FCR depicted in FIG. 11L. Alternatively, the CST comparison step 306 can also correlate the motor unit spike trains 912 rather than the CSTs 1002.

Furthermore, the CST comparison step 306 can determine the correlated signals as the cross-correlations of the CSTs 1002 for each of the agonist/antagonist muscle pairs. In addition, the CST comparison step 306 can also auto-correlate and cross-correlate each of the motor unit spike trains 912. Of importance, the cross-correlation between agonist/antagonist muscles on the same limb can provide indications of Parkinson's and pre-Parkinson's symptoms prior to any symptoms being observable.

Illustratively, the right ECR and the right FCR, shown in FIG. 11J, and its inverse in FIG. 11K, are shown to exhibit a periodic and synchronous signal indicating Parkinson's or pre-Parkinson's symptoms are present. Similarly, the left ECR and the left FCR, shown in FIG. 11B, and its inverse in FIG. 11E, are shown to exhibit no periodic or synchronous signal indicating Parkinson's or pre-Parkinson's symptoms are not present.

Of note, the cross-correlations between the left and right ECR or the left and right FCR generally exhibit little to no correlation because Parkinson's resting tremors do to exhibit tremors together. Once each of the auto-correlations and the cross-correlations, of FIG. 11A-FIG. 11L, are determined, the neuromuscular assessment system 100 can execute a report step 308.

The report step 308 can identify important pre-Parkinson's neurodegeneration information of the CSTs 1002 and the motor unit spike trains 912. Illustratively, for example this pre-Parkinson's neurodegeneration information can include a synchronicity 310 and a periodicity 312 calculated from the CSTs 1002 or the motor unit spike trains 912.

The synchronicity 310 can mean the degree of coordinated motor unit firing determined by the density of the CST 1002 or the number of individual MU spikes over a time period. One method of determining the synchronicity 310 can be based on the cross-correlation of the CSTs 1002 of agonist/antagonist muscle pairs. FIG. 11J and FIG. 11K show a high degree of synchronicity 310 between the correlated signals.

The cross-correlations of FIG. 11J and FIG. 11K are shown with periodic peaks and with a degree of synchronicity between the periodic peaks. The periodic peaks will have a smaller peak to the right of a larger peak in FIG. 11J. The distance between the peaks is indicative of the amount of synchrony or a phase shift between the input CSTs 1002 of the cross-correlation.

In one contemplated method, a synchronicity threshold 316 can be used to determine whether the correlated signals are synchronized. If the horizontal timing distance between peaks is smaller than the synchronicity threshold 316 then the signals can be considered synchronized. If the distance between peaks is the same or larger than the synchronicity threshold 316 then the signals can be considered not synchronized.

The synchronicity 310 provides an indication of when the motor unit spike trains 912 or the CSTs 1002 began and ended relative to each other. A Parkinson tremor is synchronous while a voluntary muscle movement is asynchronous. Other methods to determine the synchronicity 310 are contemplated including a coherence analysis or phase analysis of the cross-correlated wave forms of the CSTs 1002 or the motor unit spike trains 912, in order to determine the movement of signal phases in time and in relation to each other.

One contemplated method of determining the periodicity 312 of cross-correlated signals can include calculating the power spectral density for each cross-correlation. Peaks will be observed at periodic frequencies within the correlated signals.

If no frequency is identifiable in the power spectral density, then the signal can be considered not periodic, otherwise if a frequency is found with the power spectral density of correlated signals, then periodicity is found. As will be appreciated, when the correlated CSTs 1002 or the motor unit spike trains 912 is periodic, an oscillation will be observed and identified in the correlation coefficients based on lag.

When both synchronicity 310 and periodicity 312 are found a resting tremor can be identified within the correlated signals, whether the correlation is between the CSTs 1002 or the motor unit spike trains 912. During the report step 308 a tremor amplitude 318 can also be calculated.

The tremor amplitude 318 can be a magnitude of the auto-correlation or cross-correlation waveform spikes. That is, the vertical distance from a minimum trough value to a maximum peak value can be considered the tremor amplitude 318.

During the report step 308, the neuromuscular assessment system 100 can further determine a tremor frequency 320. The tremor frequency 320 can be determined by taking the power spectral density of correlated signals. The power spectral density of correlated signals can have peaks at periodic frequencies. The dominant peak is chosen for the tremor frequency 320.

During the report step 308, the neuromuscular assessment system 100 can further determine an antagonist tremor fraction 322. The antagonist tremor fraction 322 can be the percentage of correlated signals of agonist/antagonist muscle pairs determined to show resting tremor.

Figure 3B:
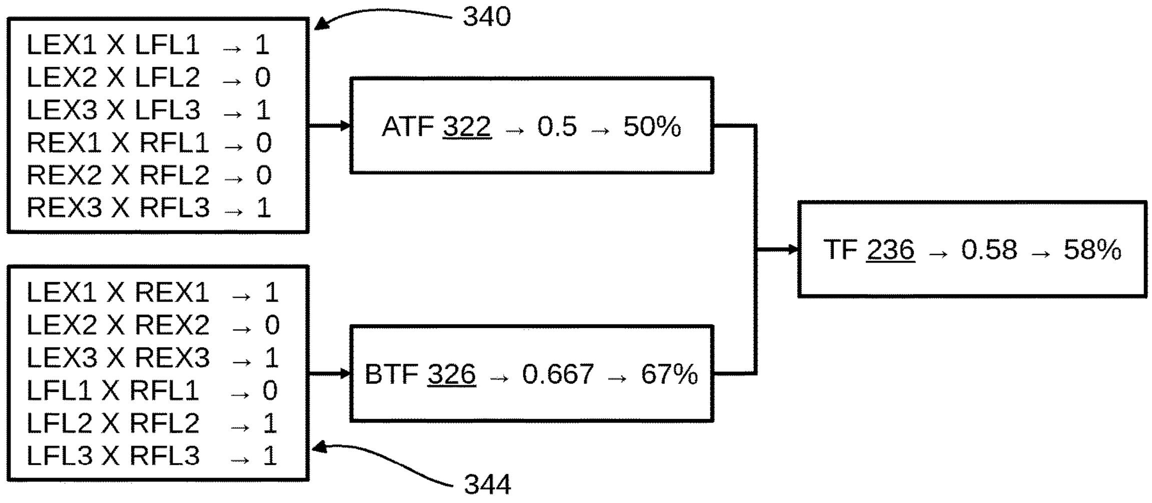
FIG. 3B is a flow chart for computing the tremor fractions of FIG. 3A.

In other words, the percentage of correlated signals for agonist/antagonist muscle pairs that are determined to have both the synchronicity 310 and the periodicity 312 will be the antagonist tremor fraction 322. This calculation is depicted in FIG. 3B for example.

During the report step 308, the neuromuscular assessment system 100 can further determine a bilateral tremor fraction 326. The bilateral tremor fraction 326 can be the percentage of correlated signals of similar muscles from both the left and right side of the body determined to show resting tremor.

In other words, the percentage of correlated signals for similar muscles from both the left and right side of the body can be for example the cross-correlation between the left ECR 802 of FIG. 8 and the right ECR 806 of FIG. 8, for example. The percentage of correlated signals for similar muscles from both the left and right side of the body that are determined to have both the synchronicity 310 and the periodicity 312 will be the bilateral tremor fraction 326. This calculation is depicted in FIG. 3B for example.

During the report step 308, the neuromuscular assessment system 100 can further determine the tremor fraction 236. The tremor fraction 236 can be the total percentage of cross-correlated signals determined to show resting tremor.

In other words, the percentage of cross-correlated signals that are determined to have both the synchronicity 310 and the periodicity 312 will be the tremor fraction 236. This calculation is depicted in FIG. 3B for example. The tremor fraction 236 over time can be reported as the Parkinson's progression score 234 of FIG. 2.

It is to be understood that the synchronicity 310, the periodicity 312, the tremor amplitude 318, the tremor frequency 320, the antagonist tremor fraction 322, the bilateral tremor fraction 326, and the tremor fraction 236 are to be considered pre-Parkinson's neurodegeneration information.

Another aspect of the neuromuscular assessment system 100 can be a convolutional neural network 332. The convolutional neural network 332 can be a continuous learning algorithm having the individual motor unit spike trains 912 as inputs and the tremor fraction 236 as an output.

It is contemplated that the convolutional neural network 332 can include hidden layers employing a sigmoid activation function, which provides results from 0 to 1 and is useful to predict probabilities such as the total tremor fraction 330. Furthermore, the hidden layers can employ a hyperbolic tangent (tanh) activation function for hidden states.

Still further, the hidden layers can employ a softmax activation function, which is contemplated to determine the non-co-occurrence in the MUAPs 920 of FIG. 9. Yet still further, error can be computed using the mean absolute error activation function. The recurrent units occur in hidden layers.

Referring now to FIG. 3B, therein is shown a flow chart for computing the tremor fractions of FIG. 3A. The neuromuscular assessment system 100 of FIG. 1 is shown with the report step 308 of FIG. 3A comparing agonist/antagonist muscle pairs on the same limb in an agonist comparison step 340.

Figure 9B:
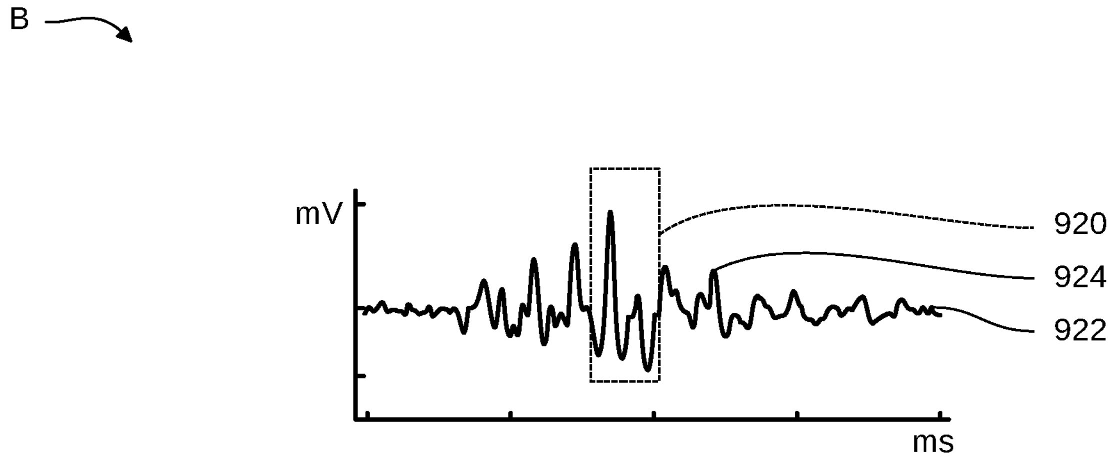
FIG. 9B is an enlarged view of area 9B of FIG. 9A.
Figure 10:
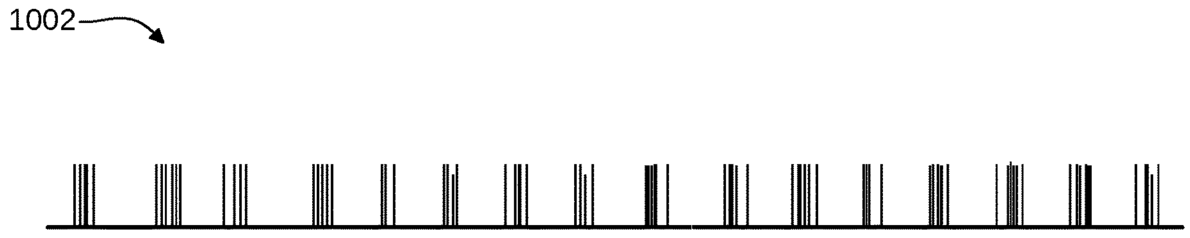
FIG. 10 is a graphical depiction of a cumulative spike train (CST) for the calculate neural drive step of FIG. 3A.

The agonist comparison step 340 includes the cross-correlation of the CSTs 1002 of FIG. 10 or the motor unit spike trains 912 of FIG. 9 from agonist/antagonist muscle pairs on the same limb. Particularly in the agonist comparison step 340, a first left extensor is correlated with a first left flexor.

Similarly, second and third agonist/antagonist muscle pairs are shown correlated for the left side. A first right extensor is correlated with a first right flexor and the second and third agonist/antagonist muscle pairs are shown correlated for the right side.

The correlated signals determined to have both the synchronicity 310 of FIG. 3A and the periodicity 312 of FIG. 3A will be considered to be a resting tremor and identified with a 1. Correlated signals without either synchronicity 310 or periodicity 312 are not considered a resting tremor and identified with a 0. Here, three out of six of the correlated signals are identified to show tremor, and thus the antagonist tremor fraction 322 is calculated to be a percentage of the correlated signals determined to have both the synchronicity and the periodicity, or 0.5, or 50%.

The neuromuscular assessment system 100 is further shown in the report step 308 correlating signals of similar muscles from both the left and right side of the body in a bilateral comparison step 344. Continuing with the same 3×3 example from above, the bilateral comparison step 344 can be a cross-correlation of the CSTs 1002 or the motor unit spike trains 912 for similar muscles from opposite sides of the body.

Particularly in the bilateral comparison step 344, a first left extensor is correlated with a first right extensor. Similarly, second and third extensors are shown correlated between the left side and right side of the body. A first left flexor is correlated with a first right flexor. Similarly, second and third flexors are shown correlated for the left side and right side of the body.

The correlated signals determined to have both the synchronicity 310 and the periodicity 312 will be considered to be a resting tremor. Here, four out of six of the correlated signals are identified to show tremor, and thus the bilateral tremor fraction 326 is calculated to be a percentage of the correlated signals determined to have both the synchronicity and the periodicity, or 0.667 or 67%.

Once the bilateral tremor fraction 326 and the antagonist tremor fraction 322 are calculated the total tremor fraction 330 can also be calculated. Illustratively, the total tremor fraction 330 can be the total percentage of the cross-correlated signals determined to have both the synchronicity and the periodicity from both the agonist comparison step 340 and the bilateral comparison step 344.

Here, the total tremor fraction 330 is the total percentage of the cross-correlated signals determined to have both the synchronicity and the periodicity, or 0.58 or 58%. The total tremor fraction 330 over time can be reported as the Parkinson's progression score 234 of FIG. 2.

Referring now to FIG. 4, therein is shown a side view of the lower arm 122 of FIG. 1. The lower arm 122 is depicted as a right lower arm having the combination sensors 104 affixed thereto. It is contemplated that the combination sensors 104 can be affixed to agonist/antagonist muscle pairs on the palm, wrist, forearm, or a combination thereof.

Particularly, the combination sensors 104 can include a first combination sensor 402 and a second combination sensor 404. Each of the combination sensors 104 can include the HD-sEMG 206, the IMU 216, and the PPG sensor 218.

The HD-sEMG 206 can include multiple electrodes 406 with a known and fixed distance 408 between each of the electrodes 406. The electrodes 406 can be arranged in a grid configuration. Here, the electrodes 406 are shown in a five by thirteen grid configuration.

The electrodes 406 can be set within an electrode carrier 410. It is contemplated that the electrode carrier 410 can be a Polyimide material roughly 50 μm thick.

It is further contemplated that the electrodes 406 can be a silver or a silver chloride material providing an impedance between skin 412 and the electrode 406 of about five Kilo-ohms. In a worst case scenario, the impedance could reach one Mega-ohm and maintain functionality.

The electrodes 406 themselves are contemplated to have a small diameter of less than three to five millimeters. Furthermore, the fixed distance 408 between the electrodes 406 should be less than eight to ten millimeters.

It is contemplated that the combination sensors 104 can be placed on multiple different agonist/antagonist muscle pairs on the lower arm 122 when targeting the resting tremor. Here, the first combination sensor 402 is shown affixed to the skin 412 over an FCR 414 while the second combination sensor 404 is affixed to the skin 412 over an ECR 416.

The components box 102 can be communicatively coupled to the combination sensors 104 and can communicate the combination sensor output signal 108 of FIG. 1 to the components box 102. It is alternatively contemplated that the components box 102 could be formed integrally with one or more of the combination sensors 104, which can reduce the amount of wiring needed.

The HD-sEMG 206 can provide multiple EMG channels of FIG. 9A with each EMG signal channel generated by electrodes 406 closely spaced at the fixed distance 408 on the skin of the patient 120 of FIG. 1. The multiple EMG channels contained within the HD-sEMG signal 208 can be analyzed within the processor 112 of FIG. 1 and provide the neural drive signal 210.

It has been discovered that utilizing the multiple electrodes 406 arranged in a grid with the fixed distance 408 enables the spatial dimension of the neural drive signal 210 to be generated for each of the MUAPs 920 of FIG. 9B. The discovery further enables the neural drive signal 210 to be evaluated for Parkinson's and pre-Parkinson's information before the symptoms become observable by a physician.

Referring now to FIG. 5, therein is shown an isometric view of the neuromuscular assessment system 100 of FIG. 1. The neuromuscular assessment system 100 is shown having the combination sensor 104 near muscle fibers 502. It will be understood that the combination sensor 104 is coupled to the skin of the patient 120 of FIG. 1 and indirectly coupled to the muscle fiber 502.

The muscle fiber 502 can be a muscle fiber within the ECR 416 of FIG. 4 or the FCR 414 of FIG. 4. The combination sensor 104 is shown in an alternative configuration from the configuration shown in FIG. 4 with the electrodes 406 distributed along two rows, or alternatively could be two electrodes 406.

The combination sensor 104 is shown further including the PPG sensor 218 and the IMU 216. The combination sensor 104 can provide the combination sensor output signal 108 of FIG. 1 through the wireless transmission 106 to the components box 102. More particularly, the combination sensor 104 can provide the HD-sEMG signal 208 having the multiple EMG channels of FIG. 9A.

The combination sensor 104 can also provide the PPG signal 222 and the IMU signal 220 to the components box 102 through the wireless transmission 106. The muscle fiber 502 can be innervated by a motor neuron 504 extending between a spinal cord 506 of the patient 120 and the muscle fiber 502.

Together the motor neuron 504 and the muscle fiber 502 can comprise a motor unit 508. Each innervation of the motor unit 508 can be one of the MUAPs 920 of FIG. 9B. The MUAPs 920 for each motor unit 508 are depicted as the motor unit spike trains 912 of FIG. 9A and the motor unit spike trains 912 for multiple motor units 508 within a muscle can be the CST 1002 of FIG. 10.

It is contemplated that the electrodes 406 should be small with a diameter of less than three to five millimeters, should be eight to ten millimeters apart, and should be placed distal to the innervation zone.

Figure 6:
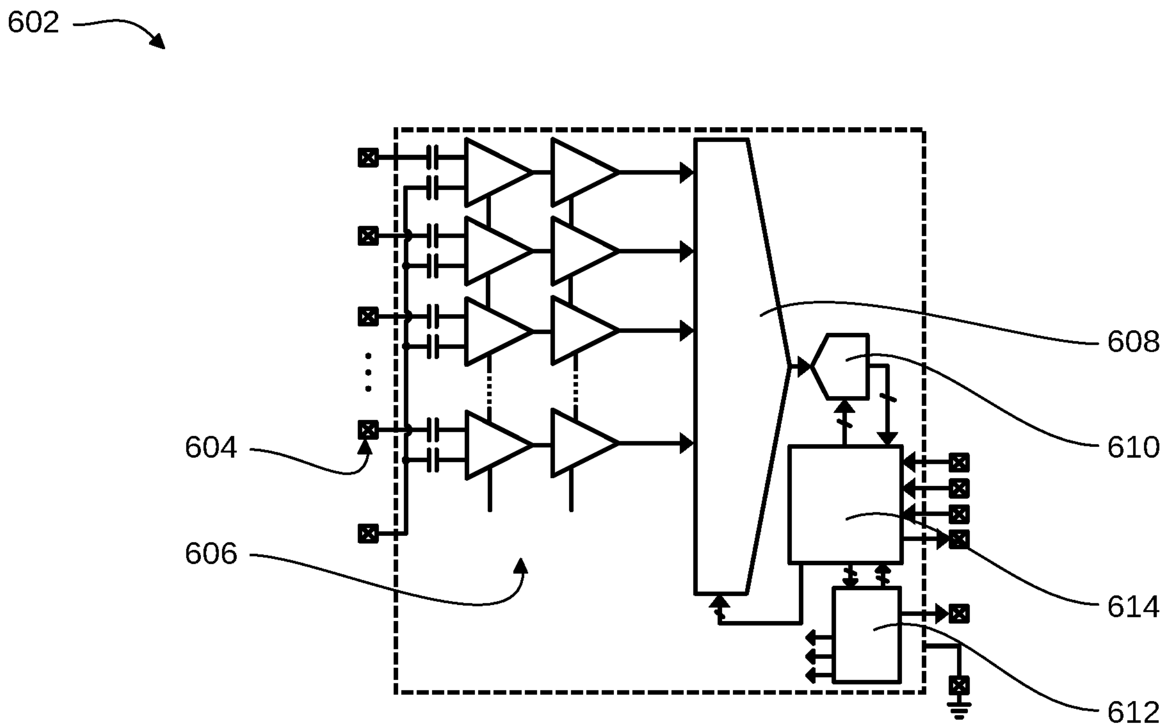
FIG. 6 is a schematic view of an analog front end (AFE) for use with the neuromuscular assessment system of FIG. 1.

Referring now to FIG. 6, therein is shown a schematic view of an analog front end 602 (AFE) for use with the neuromuscular assessment system 100 of FIG. 1. The electrodes 406 of FIG. 4 or of FIG. 5 can be coupled directly or indirectly to inputs 604 of the AFE 602.

It is contemplated that each of the electrodes 406 would be coupled to an individual one of the inputs 604. Therefore, the AFE 602 is contemplated to have enough inputs 604 to accommodate a direct connection to each one of the electrodes 406 in an array, for example, the array disclosed in FIG. 4.

The inputs 604 can be coupled to multistage amplifiers 606, which amplify the EMG channels of FIG. 9A. Prior to amplification, the EMG signal channels can be DC filtered with capacitors between the electrodes 406 and the multistage amplifiers 606. The output of the multistage amplifiers 606 can be amplified EMG signals that can be input into an analog multiplexer 608.

The output of the analog multiplexer 608 can be digitized utilizing an analog to digital converter 610. The digitized EMG signals can be stored in a digital registry 612, which can be the non-transitory computer readable medium 110 of FIG. 1. The AFE 602 can be controlled with a digital controller 614 having a serial peripheral interface providing a synchronous serial communication.

Figure 7:
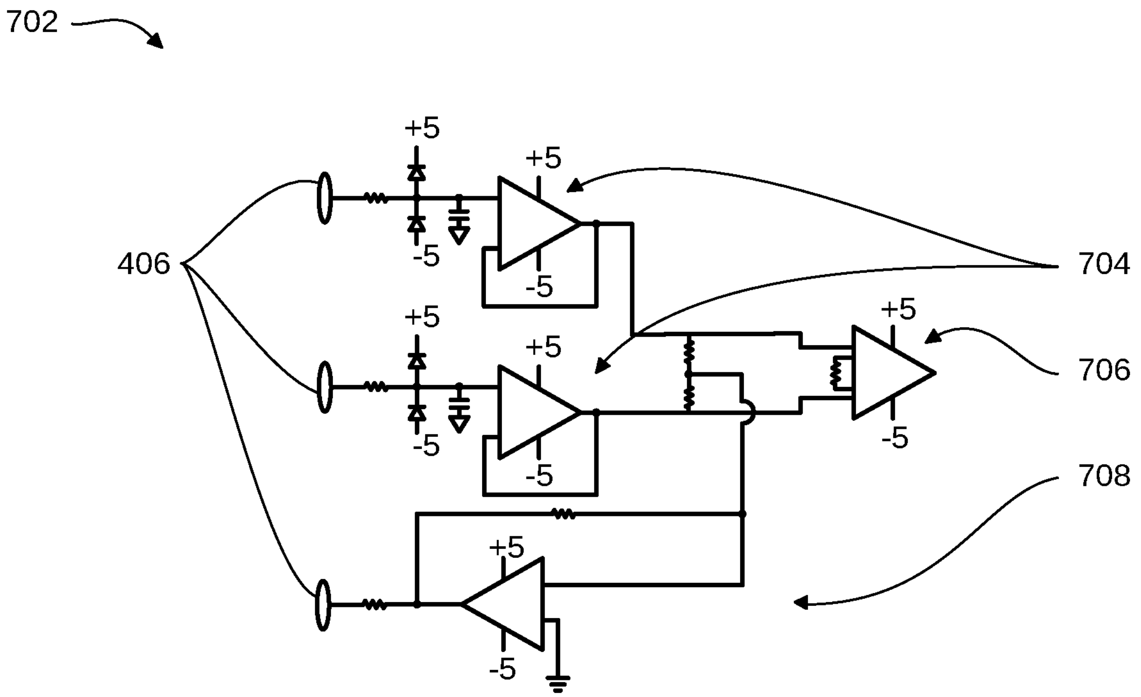
FIG. 7 is a schematic view of a surface Electromyography (sEMG) amplifier for use with the neuromuscular assessment system of FIG. 1.

Referring now to FIG. 7, therein is shown a schematic view of an sEMG amplifier 702 for use with the neuromuscular assessment system 100 of FIG. 1. The sEMG amplifier 702 can be used as a buffer for low input bias current into the AFE 602 of FIG. 6, as the input bias current of the AFE 602 can polarize the electrode if there is poor contact between the electrodes 406 and the patient 120.

The sEMG amplifier 702 can include junction field effect transistor input operational amplifiers (JFET input op amps 704) that have input bias currents of less than 1 pico-amp. The sEMG amplifier 702 is contemplated to have enough JFET input op amps 704 to accommodate a direct connection to each one of the electrodes 406 in an array, for example, the array disclosed in FIG. 4.

A second JFET input instrumentation amplifiers 706 can have input bias currents under 20 pico-amps. It is contemplated that the input impedance for the sEMG amplifier 702 should be at least 100 times greater than the largest expected resistance between the electrodes 406 and the patient 120 of FIG. 1.

The impedances between the skin of the patient 120 of FIG. 1 and the electrodes 406 at ten hertz using silver or silver chloride electrodes and with the skin properly prepared, are typically about five Kilo-ohms however in the worst case, this impedance is about one Mega-ohm.

The electrodes 406 should be small with a diameter of less than three to five millimeters, be arranged with a distance of less than eight millimeters apart, and placed, distal to the innervation zone of the muscle fiber 502 of FIG. 5.

Here, the JFET input op amps 704 are contemplated to have an input impedance of greater than 100 Mega-ohms, a common mode rejection of over 100 dB, a gain of one thousand, and a bandwidth of greater than one Kilo-hertz. A driven right leg 708 can drive a common mode voltage back to the skin of the patient 120. The feedback loop of the driven right leg 708 improves the common mode rejection by an amount equal to one plus the closed-loop gain of the driven right leg 704.

Referring generally to FIG. 8A through FIG. 8D, these FIGs. serve as a useful illustration of the multiple combination sensor output signals 108 of FIG. 1 for the early identification of resting tremor. The combination sensor output signals 108 will include signals for one of the combination sensors 104 of FIG. 1 on the left arm 124 of FIG. 1 and the right arm 126 of FIG. 1.

More particularly, the combination sensor output signals 108 will include signals for the first combination sensor 402 of FIG. 4 and the second combination sensor 404 of FIG. 4 coupled to the right arm 126 as depicted in FIG. 4 and will further include two additional combination sensors 104 coupled to the ECR 416 of FIG. 4 and the FCR 414 of FIG. 4 on the left arm 124 of the patient 120 of FIG. 1. For ease of description, ellipses are used to depict more readings from an individual combination sensor 104 when used with regard to the electrode arrays and depict more readings from a different combination sensor 104 on the same arm when used with regard to the IMU signal 220 of FIG. 2 and the PPG sensor 218 of FIG. 2.

Referring now to FIG. 8A, therein is shown a graphical depiction of the HD-sEMG signal 208 of the combination sensor 104 of FIG. 1. The HD-sEMG signal 208 can include an HD-sEMG signal for the electrode array of the combination sensors 104 for the left ECR 802, the left FCR 804, the right ECR 806, and the right FCR 808.

For descriptive clarity, the full array of the HD-sEMG signal 208 for each of the ECR's and FCR's is not shown. The vertical axis can be a measurement of volts, providing one millivolt per division. The horizontal axis can be a measurement of time, providing two hundred milliseconds per division.

Resting tremor involves a low frequency component of the neural drive which is bi-laterally asymmetric and asynchronous by alternating between agonist and antagonist muscles on the same limb. Less commonly resting tremors can be synchronous between agonist and antagonist muscles.

This can be expressed in later stages of Parkinson's as a shaking of an arm on one side of the body. The bi-lateral asymmetry is depicted by the HD-sEMG signals 208 for the right ECR 806 and the right FCR 808 showing little activity while the left ECR 802 and the left FCR 804 show activity.

Furthermore, the alternating character is depicted within a first time window 810 and a second time window 812. Illustratively, the time window 810 shows the alternating activation as an activation in the left ECR 802 and little in the left FCR 804 while the time window 812 shows the alternating activation as activation in the left FCR 804 and little in the left ECR 802.

In later stages of Parkinson's disease, the bi-laterally asymmetry and the agonist/antagonist alternation can be observed in the EMG readings or by visually observing the patient 120 of FIG. 1. However, early stage and pre-Parkinson's symptoms are not so easily identifiable but are detectable with the methods proposed herein.

That is, the array of the electrodes 406 of FIG. 4 can provide a spatial dimension to the data allowing neural drive signals 210 of FIG. 2 to be generated and to thereby generate pre-Parkinson's disease information of pre-Parkinson's and early pre-Parkinson's disease, which are not obtainable by previous developments in the art.

Figure 8B:
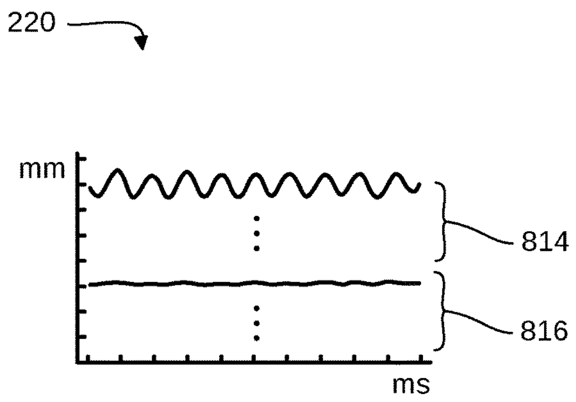
FIG. 8B is a graphical depiction of the IMU signals of the combination sensors of FIG. 1.

Referring now to FIG. 8B, therein is shown a graphical depiction of the IMU signals 220 of the combination sensors 104 of FIG. 1. The IMU signals 220 can include a left acceleration 814 and a right acceleration 816 corresponding to the combination sensors 104 of FIG. 1 coupled to the left arm 124 of FIG. 1 and the right arm 126 of FIG. 1, respectively.

For descriptive clarity only a single IMU signal 220 is shown for the left arm 124 and the right arm 126. The vertical axis can be a measurement of physical displacement, providing one millimeter per division. The horizontal axis can be a measurement of time, providing two hundred milliseconds per division.

The bi-lateral asymmetry of the resting tremor is depicted by the IMU signal 220 showing a relatively sinusoidal displacement on the left acceleration 814 while little to no displacement is recorded for the right acceleration 816. It will be appreciated that the resting tremor will exhibit the roughly sinusoidal displacement shown in the left acceleration 814; and can be understood, together with the right acceleration 816 as being bilaterally asymmetric between the two sensors.

Figure 8C:
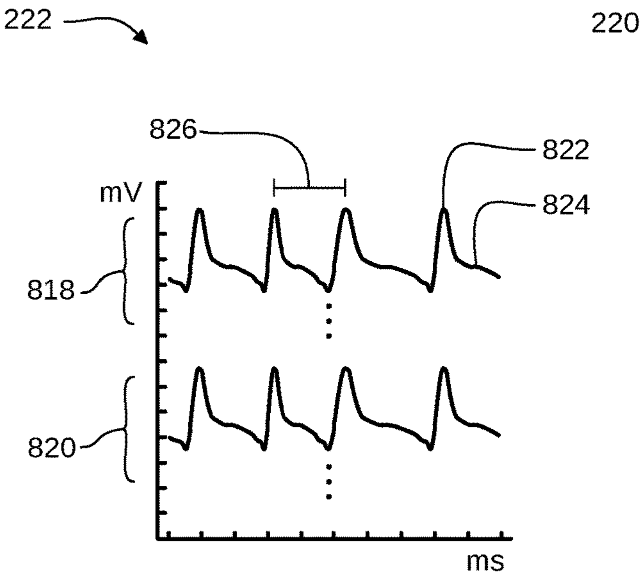
FIG. 8C is a graphical depiction of the Photoplethysmography (PPG) signals of the combination sensors of FIG. 1.

Referring now to FIG. 8C, therein is shown a graphical depiction of the PPG signals 222 of the combination sensors 104 of FIG. 1. The waveform of the PPG signals 222 is produced by variations in the attenuation of a light energy as it passes through, is scattered and reflected within, or is absorbed by biological tissues prior to being detected with an optical sensor.

The PPG signal 222 can include a left PPG signal 818 and a right PPG signal 820 corresponding to the combination sensors 104 of FIG. 1 coupled to the left arm 124 of FIG. 1 and the right arm 126 of FIG. 1, respectively.

For descriptive clarity only a single PPG signal 222 is shown for the left arm 124 and the right arm 126. The vertical axis can be a measurement of volts, providing one tenth of a millivolt per division. The horizontal axis can be a measurement of time, providing two hundred milliseconds per division.

Analysis of the PPG signal 222 within the signals block 204 of FIG. 2 can provide an indication of the blood pressure 224 of FIG. 2 with an estimation of a systole pulse wave 822 and diastole pulse wave 824. Further, a time interval between systole pulse waves 822 can be determined, from which the heart rate 225 of FIG. 2 and the heart rate variability 226 of FIG. 2 can be derived.

For example, the heart rate 225 can be sixty divided by the time in seconds between systole pulse waves 826. The heart rate variability 226 can be computed from the heart rate 225 or directly from the systole pulse waves 822. The heart rate variability 226 is an early indicator of Parkinson's disease but is not adequately specific by itself. It is contemplated therefore to combine the heart rate variability 226 with the HD-sEMG signals 208 of FIG. 2 to advance specificity.

Figure 8D:
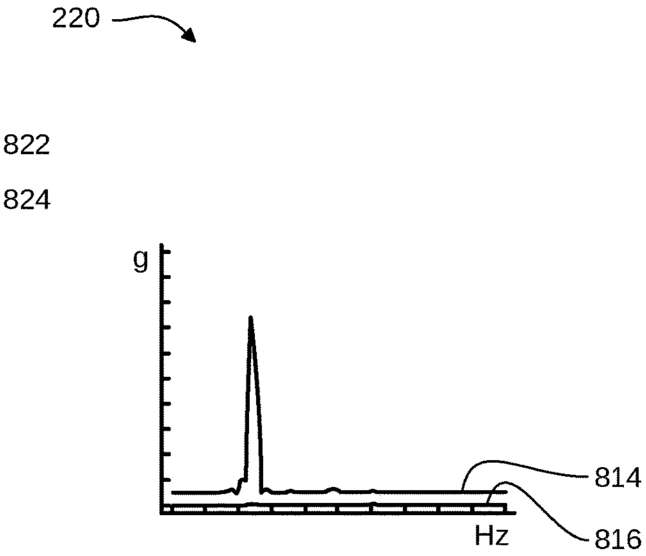
FIG. 8D is a graphical depiction of the IMU signal of FIG. 8B in the frequency domain.

Referring now to FIG. 8D, therein is shown a graphical depiction of the IMU signal 220 of FIG. 8B in the frequency domain. For ease of description, the IMU signals 220 only include the left acceleration 814 and the right acceleration 816 shown in FIG. 8B.

The vertical axis can be a measurement of acceleration or G-force, providing 6×10^-4 g^2 per division. The horizontal axis can be a measurement of frequency, providing two hertz per division.

The bi-lateral asymmetry of the resting tremor is depicted by the IMU signal 220 showing a spike in acceleration between 4 Hz and 6 Hz. This corresponds to a relatively sinusoidal displacement for the left arm 124 of FIG. 1 while experiencing a resting tremor while little to no spikes are observed in the right acceleration 816.

A sinusoidal bonus can be added to the Parkinson's propensity score 232, the tremor fraction 236, the freeze of gait fraction 238, and the Parkinson's progression score 234, all of FIG. 2. The sinusoidal bonus could, for example, be an increase in ten percentage points if the sinusoidal wave is detected showing a spike in acceleration between 4 Hz and 6 Hz.

Referring now to FIG. 9A, therein is shown a graphical depiction of a decomposition process 900 for the calculate neural drive step 304 of FIG. 3A. The decomposition process 900 first includes receiving the HD-sEMG signals 208 of FIG. 2 for each of the electrodes 406 of FIG. 4 for one of the combination sensors 104 of FIG. 1. For clarity, ellipses are used to depict more HD-sEMG signals 208 from other electrodes 406 in the array for an individual combination sensor 104.

Illustratively, for example, the surface EMG reading from each of the electrodes 406 can be an EMG channel. Here, a first EMG channel 902, a second EMG channel 904, a third EMG channel 906, and a nth EMG channel 908 are shown. It is contemplated that tens or hundreds of EMG channels could be provided by each of the combination sensors 104.

Individual Motor Unit Action Potentials (MUAPs 920 of FIG. 9B) travel through motor units, such as the motor unit 508 of FIG. 5. The MUAPs 920 are detected with different electrodes 406 within the array of the combination sensor 104, and due to the fixed distance 408 of FIG. 4 between the electrodes 406, the MUAPs 920 will be detected with differences in the shape of the waveforms between the electrodes 406.

MUAPs 920 closer to the electrodes 406 will be detected with more intensity than the MUAPs 920 further from the electrode 406. These MUAPs 920 of various intensities from multiple different motor units 508, along with noise, can mix together and be detected together by a single electrode 406 as one of the channels from the first EMG channel 902 through the nth EMG channel 908.

It is contemplated that the HD-sEMG signals 208 can be decomposed using multiple available methods from older template driven decompositions to modern recurrent neural networks within the processor 112 of FIG. 1 controlled with the instructions 114 of FIG. 1. A decomposition algorithm 910 can take the HD-sEMG signals 208 as inputs and return motor unit spike trains 912.

The horizontal axis of the HD-sEMG signals 208 and the motor unit spike trains 912 could be time in seconds or milliseconds. The vertical axis of the HD-sEMG signals 208 can be voltage while the vertical axis of the motor unit spike trains 912 can be dimensionless and represent only the MUAPs 920 existing at a specific time along the horizontal.

The motor unit spike trains 912 are depicted as MU1 through MU6 corresponding to six motor units 508, the number of which is illustrative, but in practice could include any number of motor units 508 being activated with a detectable MUAP 920. Ellipses are used to depict other possible motor unit spike trains 912.

Illustratively, for example, it is contemplated that a gated recurrent neural network following a gradient convolution kernel algorithm can be employed in the decomposition process 900, which relies on a retrospective calculation based on past and present values to decompose and identify the MUAPs 920.

The architecture of a gated recurrent decomposition algorithm 910 can be formulated as:

$$rt=\sigma(Wir*xt+bir+Whr*ht-1+bhr) \quad \text{Equation 1}$$

$$zt=\sigma(Wiz*xt+biz+Whz*ht-1+bhz) \quad \text{Equation 2}$$

$$nt=\tanh(\mathrm{Win}*xt+\mathrm{bin}+rt\otimes(Whn*ht-1+bhn)) \quad \text{Equation 3}$$

$$ht=(1-zt)\otimes nt\otimes ht-1 \quad \text{Equation 4}$$

where xt and ht−1 are respectively the input vector at time t and the hidden vector from the previous timestep. rt, zt and nt are respectively the reset, update, and new gate vectors. The output of the unit ht is the new hidden vector, which is also the newoutput vector. The gates are parameterized by the weights W and biases b. σ and tanh are the sigmoid and hyperbolic tangent activation functions, whilst ⊗ is the Hadamard product.

Common elements are decomposed and identified, and each decomposed signal corresponds to one of the motor units 508. Multiple electrodes 406 give a spatial resolution while temporal resolution comes from the decomposition process 900.

Furthermore, motor unit activation is effectively a point process and is highly unlikely to co-occur with another source. This property can be exploited by the softmax activation function:

$$\mathrm{softmax}(yi)=\exp(yj)/\sum j(yj) \quad \text{Equation 5}$$

The softmax function can convert a vector into a probability distribution and can be used as the last activation function of the decomposition algorithm 910 providing a probability distribution over predicted output classes. The Sigmoid and hyperbolic tangent functions can also be used in hidden layers of the decomposition algorithm 910.

The motor unit spike trains 912, MU6 through MU1, can be a collection of the MUAPs 920 generated by one motor unit 508 and shown as motor unit action potential spikes 914. The motor unit action potential spikes 914 are positioned at their times of occurrence or separated by their inter-discharge intervals 916. As such, the temporal resolution is maintained within the motor unit spike train 912 and spatial resolution is provided by identifying each of the different motor units 508 innervated by each of the action potential spikes 914.

The decomposition algorithm 910 requires the HD-sEMG signals 208 as inputs and return motor unit spike trains 912 as outputs. This process cannot practically be performed in the human mind, for instance the human mind is not equipped to receive the HD-sEMG signals 208 and calculation times would limit any real world application of the decomposition algorithm 910. The decomposition algorithm 910 could not, as a practical matter, be performed entirely in a human's mind.

Furthermore, the decomposition algorithm 910 requires the manipulation of computer data structures (e.g., the HD-sEMG signals 208) and the output of a motor unit spike train 912, which as a practical matter cannot be performed entirely in a human's mind. Yet further, the auto-correlations and the cross-correlations of the motor unit spike trains 912 and the CSTs 1002 of FIG. 10 requires the manipulation of computer data structures that could not, as a practical matter, be performed entirely in a human's mind.

Prior Parkinson's monitoring developments have a deep rooted technical problem that these prior developments were not capable of using and did not use neural drive data, such as the motor unit spike trains 912 and the CSTs 1002 for generating Parkinson's or pre-Parkinson's disease information. These technical problems were magnified as the prior developments did not analyze the neural drive data.

Here, the use of the neural drive data provides a solution rooted in technology to solve this technical problem and also provides the new ability to generate the pre-Parkinson's disease information from early neural drive data without waiting for the expression of conspicuous symptoms, which has been a long felt need in the monitoring industry.

The neural drive data should be considered functional data recognized by the neuromuscular assessment system 100 for the purpose of generating the pre-Parkinson's disease information and the neural drive data. The neural drive data also determines the technical ability and the internal operation of the neuromuscular assessment system 100 in the generation of the pre-Parkinson's disease information.

The format of the neural drive data as spike trains or cumulative spike trains is functional inherently comprise, or reflect, corresponding technical features of the neuromuscular assessment system 100. That is the neural drive data reflects the physical collection through the electrode arrays and the decomposition of raw signals into spike trains.

Referring now to FIG. 9B, therein is shown an enlarged view of area B of FIG. 9A. The area 9B can depict a MUAP 920.

The MUAP 920 can be a single motor unit action potential distorted by noise 922 and other MUAPs 924 present and detectable by one of the electrodes 406 of FIG. 4. The horizontal axis can be a measurement of time providing divisions in milliseconds, while the vertical axis can be a measurement of voltage providing divisions in millivolts.

Referring now to FIG. 10, therein is shown a graphical depiction of cumulative spike train (CST) 1002 for the calculate neural drive step 304 of FIG. 3A. Once the motor unit spike trains 912 of FIG. 9 are calculated, the motor unit spike trains 912 can be summed to calculate and determine the CST 1002.

The motor unit spike trains 912 and the CSTs 1002 are to be understood herein as neural drive data. The CST 1002 can be the total neural drive to a muscle, which is the sum of individual motor unit spike trains into the CST 1002.

The CST 1002 can then be low pass filtered to preserve frequencies below a lowpass filter threshold, such as below 20 hertz. The low pass filter can isolate the resting tremor, which is a low frequency occurrence.

Referring now to FIG. 11A through FIG. 11L, which depict all combinations of auto-correlation and cross-correlation that can be computed between the CSTs 1002 of FIG. 10 for the left ECR 802, the left FCR 804, the right ECR 806, and the right FCR 808, all of FIG. 8. The vertical axis of FIG. 11A through FIG. 11L can be a dimensionless number between −1 and +1 indicating the degree of correlation. The horizontal axis of FIG. 11A through FIG. 11L can be a measurement of time lag from −1 second to +1 second.

Importantly, the cross-correlation between agonist/antagonist muscle pairs on the same arm can be both periodic and synchronous if Parkinson's or pre-Parkinson's symptoms are present. The cross-correlation of the agonist/antagonist muscle pairs are shown in FIG. 11B, FIG. 11E, FIG. 11J, and FIG. 11K.

Innervation patterns of the input CSTs 1002 can have a degree of asynchrony when the innervation of the agonist/antagonist muscles do not start or end at the same time, which is also described as a phase shift in the input CSTs and which the synchronicity threshold 316 of FIG. 3A accounts for. Innervation patterns of the input CSTs 1002 can have a periodic correlation when the innervation of the agonist/antagonist muscle pair occurs repeatedly over time.

Referring now to FIG. 11A, therein is shown a graphical depiction of a CST auto-correlation for the left ECR 802 of FIG. 8A. The CST 1002 of FIG. 10 for the left ECR 802 is auto-correlated with itself and exhibits the classical peak of an auto-correlation.

Referring now to FIG. 11B, therein is shown a graphical depiction of a CST cross-correlation between the left ECR 802 of FIG. 8A and the left FCR 804 of FIG. 8A. As previously noted, the cross-correlation between agonist/antagonist muscle pairs on the same arm can be both periodic and synchronous if Parkinson's or pre-Parkinson's symptoms are present.

Here, the cross-correlation between the CST 1002 of the left ECR 802 and the CST 1002 of the left FCR 804 do not show peaks, which indicate no correlation between the input CSTs 1002. Parkinson's resting tremors are not generally expressed on both sides of the patient 120 of FIG. 1 at the same time.

Therefore, innervations of the agonist/antagonist muscles on one side of the patient's 120 body that do not show periodic and synchronous correlation might not rule out Parkinson's symptoms because the periodic and synchronous correlation may be present on the other side of the patient's 120 body. The relationship between the CST 1002 of the left ECR 802 and the CST 1002 of the left FCR 804 are mirrored between the cross-correlation of FIG. 11B and FIG. 11E.

Referring now to FIG. 11C, therein is shown a graphical depiction of a CST cross-correlation between the left ECR 802 of FIG. 8A and the right ECR 806 of FIG. 8A. The CST 1002 of the left ECR 802 and the CST 1002 of the right ECR 806 are depicted with little to no correlation because Parkinson's resting tremors are asymmetric, not generally being expressed on both sides of the patient 120 of FIG. 1 at the same time. The inverse CST cross-correlation between the right ECR 806 and the left ECR 802 can also be computed and evidence a similar lack of correlation, but is not reproduced for ease of description.

Referring now to FIG. 11D, therein is shown a graphical depiction of a CST cross-correlation between the left ECR 802 of FIG. 8A and the right FCR 808 of FIG. 8A. The CST 1002 of the left ECR 802 and the CST 1002 of the right FCR 808 are depicted with little to no correlation because Parkinson's resting tremors are asymmetric, not generally being expressed on both sides of the patient 120 of FIG. 1 at the same time. The inverse CST cross-correlation between the right FCR 808 and the left ECR 802 can also be computed and evidence a similar lack of correlation, but is not reproduced for ease of description.

Referring now to FIG. 11E, therein is shown a graphical depiction of a CST cross-correlation between the left FCR 804 of FIG. 8A and the left ECR 802 of FIG. 8A. As previously noted, the cross-correlation between agonist/antagonist muscle pairs on the same arm can be both periodic and synchronous if Parkinson's or pre-Parkinson's symptoms are present.

Here, the cross-correlation between the CST 1002 of the left FCR 804 and the CST 1002 of the left ECR 802 do not show peaks, which indicate no correlation between the input CSTs 1002. Parkinson's resting tremors are not generally expressed on both sides of the patient 120 of FIG. 1 at the same time.

Therefore, innervations of the agonist/antagonist muscles on one side of the patient's 120 body that do not show periodic and synchronous correlation do not rule out Parkinson's symptoms because the periodic and synchronous correlation may be present on the other side of the patient's 120 body. The relationship between the CST 1002 of the left FCR 804 and the CST 1002 of the left ECR 802 are mirrored between the cross-correlation of FIG. 11B and FIG. 11E.

Referring now to FIG. 11F, therein is shown a graphical depiction of an CST auto-correlation for the left FCR 804 of FIG. 8A. The CST 1002 of FIG. 10 for the left FCR 804 is auto-correlated with itself and exhibits the classical peak of an auto-correlation.

Referring now to FIG. 11G, therein is shown a graphical depiction of a CST cross-correlation between the left FCR 804 of FIG. 8A and the right ECR 806 of FIG. 8A. The CST 1002 of the left FCR 804 and the CST 1002 of the right ECR 806 are depicted with little to no correlation because Parkinson's resting tremors are asymmetric, not generally being expressed on both sides of the patient 120 of FIG. 1 at the same time. The inverse CST cross-correlation between the right ECR 806 and the left FCR 804 can also be computed and evidence a similar lack of correlation, but is not reproduced for ease of description.

Referring now to FIG. 11H, therein is shown a graphical depiction of a CST cross-correlation between the left FCR 804 of FIG. 8A and the right FCR 808 of FIG. 8A. The CST 1002 of the left FCR 804 and the CST 1002 of the right FCR 808 are depicted with little to no correlation because Parkinson's resting tremors are asymmetric, not generally being expressed on both sides of the patient 120 of FIG. 1 at the same time. The inverse CST cross-correlation between the right FCR 808 and the left FCR 804 can also be computed and evidence a similar lack of correlation, but is not reproduced for ease of description.

Referring now to FIG. 11I, therein is shown a graphical depiction of a CST auto-correlation for the right ECR 806 of FIG. 8A. The CST 1002 of FIG. 10 for the right ECR 806 is auto-correlated with itself and exhibits the multiple classical peaks of an auto-correlation where the input CST 1002 has a periodic nature.

Referring now to FIG. 11J, therein is shown a graphical depiction of a CST cross-correlation between the right ECR 806 of FIG. 8A and the right FCR 808 of FIG. 8A. As previously noted, the cross-correlation between agonist/antagonist muscle pairs on the same arm can be both periodic and synchronous if Parkinson's or pre-Parkinson's symptoms are present.

Here, the cross-correlation between the CST 1002 of the right ECR 806 and the CST 1002 of the right FCR 808 do show multiple peaks over time indicating a correlation between repeating or periodic innervations recorded in the input CSTs 1002.

Further, each of the multiple peaks also have an asymmetry with a smaller peak to the right of a larger peak on the left. This asymmetry is indicative of the amount of synchrony or a phase shift between the input CSTs 1002 of the cross-correlation, which the synchronicity threshold 316 of FIG. 3A measures. The CST cross-correlation between the right ECR 806 and the right FCR 808 therefore indicate Parkinson's or pre-Parkinson's disease information is present in the neural drive of the patient 120 of FIG. 1.

It has been discovered that the cross-correlation between the CSTs 1002 of agonist/antagonist muscle pairs provides a solution to a long-standing technical problem with previous developments in that prior developments were limited to detecting and classifying later stage Parkinson's symptoms when treatment options are likely to narrow and increase in cost. Rather, the cross-correlation between the CSTs 1002 of agonist/antagonist muscle pairs is qualitatively different, in that, this cross-correlation evaluates the neural origin of Parkinson's resting tremors with a high degree of sensitivity enabling the generation of pre-Parkinson's disease information for resting tremors even when previous developments cannot detect or generate such information.

Although evaluation of the neural drive of a patient 120 is shown and described with regard to evaluating the CSTs 1002, the evaluation of the motor unit spike trains 912 of FIG. 9A, prior to being combined into the CSTs 1002, can provide this qualitatively new ability to assess the neural drive of the patient 120 for Parkinson's and pre-Parkinson's symptoms with a sensitivity previously unknown. The disclosed evaluation of the motor unit spike trains 912 when combined into the CSTs 1002 is for descriptive clarity only.

The amount of synchrony between the CST 1002 of the right ECR 806 and the CST 1002 of the right FCR 808 will be mirrored between the cross-correlation of FIG. 11J and FIG. 11K depicted by each of the multiple peaks having the smaller peak on a different side of the larger peak.

Referring now to FIG. 11K, therein is shown a graphical depiction of a CST cross-correlation between the right FCR 808 of FIG. 8A and the right ECR 806 of FIG. 8A. As previously noted, the cross-correlation between agonist/antagonist muscle pairs on the same arm can be both periodic and synchronous if Parkinson's or pre-Parkinson's symptoms are present.

Here, the cross-correlation between the CST 1002 of the right FCR 808 and the CST 1002 of the right ECR 806 do show multiple peaks over time indicating a correlation between repeating or periodic innervations recorded in the input CSTs 1002.

Further, each of the multiple peaks also have an asymmetry with a smaller peak to the left of a larger peak on the right. This asymmetry is indicative of a degree of synchrony or a phase shift between the input CSTs 1002 of the cross-correlation, which the synchronicity threshold 316 of FIG. 3A measures. The CST cross-correlation between the right FCR 808 and the right ECR 806 therefore enable Parkinson's or pre-Parkinson's disease information to be generated based on the neural drive of the patient 120 of FIG. 1.

It has been discovered that the cross-correlation between the CSTs 1002 of agonist/antagonist muscle pairs provides a solution to a long-standing technical problem with previous developments in that prior developments were limited to detecting and classifying later stage Parkinson's symptoms when treatment options are likely to narrow and increase in cost. Rather, the cross-correlation between the CSTs 1002 of agonist/antagonist muscle pairs is qualitatively different, in that, this cross-correlation evaluates the neural origin of Parkinson's resting tremors with a high degree of sensitivity enabling the generation of pre-Parkinson's disease information for resting tremors even when they are not observable by previous developments.

Although evaluation of the neural drive of a patient 120 is shown and described with regard to evaluating the CSTs 1002, the evaluation of the motor unit spike trains 912 of FIG. 9A, prior to being combined into the CSTs 1002, can provide this qualitatively new ability to assess the neural drive of the patient 120 for Parkinson's and pre-Parkinson's symptoms with a sensitivity previously unknown. The disclosed evaluation of the motor unit spike trains 912 when combined into the CSTs 1002 is for descriptive clarity only.

The amount of synchrony between the CST 1002 of the right FCR 808 and the CST 1002 of the right ECR 806 will be mirrored between the cross-correlation of FIG. 11J and FIG. 11K depicted by each of the multiple peaks having the smaller peak on a different side of the larger peak.

Referring now to FIG. 11L, therein is shown a graphical depiction of a CST auto-correlation for the right FCR 808 of FIG. 8A. The CST 1002 of FIG. 10 for the right FCR 808 is auto-correlated with itself and exhibits the multiple classical peaks of an auto-correlation where the input CST 1002 has a periodic nature.

Figure 12:
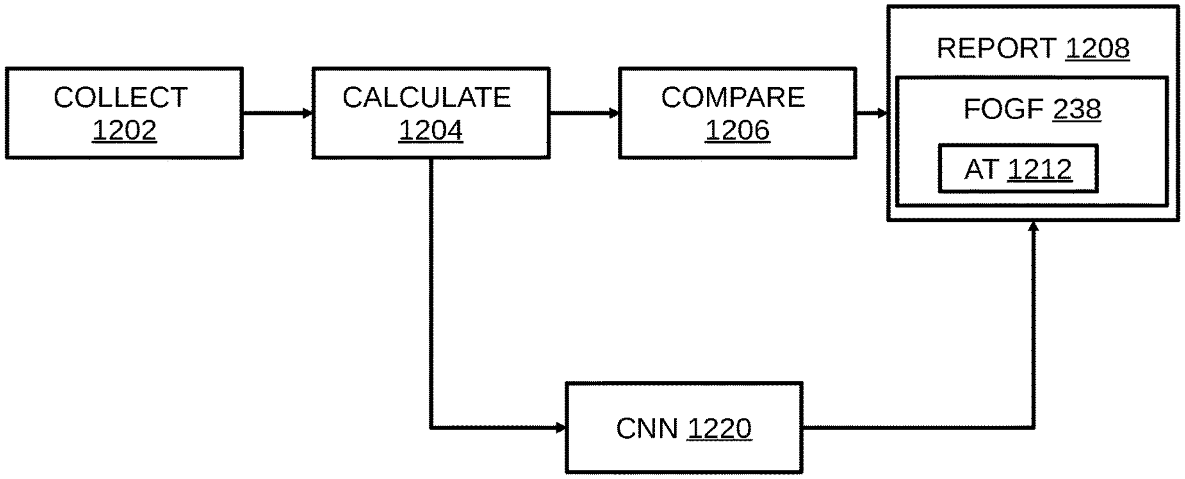
FIG. 12 is a control flow for computing freeze of gait information for the neuromuscular assessment system of FIG. 1.

Referring now to FIG. 12, therein is shown a control flow for computing freeze of gait information for the neuromuscular assessment system 100 of FIG. 1. Computing the freeze of gait information can be understood as generating pre-Parkinson's disease information. The freeze of gait information can include the freeze of gait fraction 238. The freeze of gait fraction 238 can be calculated in a way similar to the tremor fraction 236 of FIG. 2 in that the HD-sEMG signal 208 of FIG. 2 can be decomposed into the motor unit spike trains 912 of FIG. 9A.

Because this process applies to both the freeze of gait fraction 238 and the tremor fraction 236, the description of the freeze of gait fraction 238 will refer back to FIG. 9A, FIG. 10, and FIG. 11A through FIG. 11L in order to avoid duplication of these descriptions.

The neuromuscular assessment system 100 can begin to calculate the freeze of gait fraction 238 with a collection step 1202. The collection step 1202 can include placing the HD-sEMG 206 of FIG. 2 on agonist/antagonist muscle pairs from one leg, as described with regard to FIG. 1.

For monitoring freeze of gait, the Gastrocnemius muscle and the Tibialis anterior muscle work well. Freeze of gait is an abnormal gait pattern exhibiting short and temporary pauses in foot movement despite the intention to continue walking.

Technical shortcomings of previous developments lead to a failure to determine freeze of gait due to multiple challenges. For example, the MUAPs 920 of FIG. 9A are active in both standing still and freeze of gait, movements in both standing still and freeze of gait are similar, and resuming a regular gait cycle is not a sufficient indicator of absence of freeze of gait.

The technical shortcomings of previous developments include the inability to detect, isolate, and evaluate a neural drive with the HD-sEMG signals at the neural drive level of the motor unit spike trains. The collection step 1202 can include the collection of the HD-sEMG signal 208 of FIG. 2 and further shown, for example in FIG. 15A. The HD-sEMG signals 208 can be collected or stored in the non-transitory computer readable medium 110 of FIG. 1 while the collection step 1202 runs continuously.

It has been discovered that the HD-sEMG data provides richer information than traditional sEMG by providing a spatial dimension to EMG signals allowing the spatial triangulation of muscle activity and activation over time. This can be calculated as the neural drive signal 210 of FIG. 2 in a calculate neural drive step 1204.

The neural drive signal 210 can be the motor unit spike trains 912. That is, the calculate neural drive step 1204 can retrieve the HD-sEMG signal 208 from the HD-sEMG 206 and calculate the motor unit spike trains 912.

The operation of the calculate neural drive step 1204 is described in greater detail with regard to FIG. 9A and involves the decomposition of the HD-sEMG signals 208 into the MUAPs 920, which are abstracted to preserve only the spike times of the MUAPs 920 for each motor unit 508 of FIG. 5 into the motor unit spike trains 912. Once the motor unit spike trains 912 are calculated, the motor unit spike trains 912 can be summed to calculate and determine the CST 1002 of FIG. 10.

The CSTs 1002 can be calculated for each of the combination sensors 104 of FIG. 1. Continuing with the example from FIG. 1 for the lower leg 128, the calculate neural drive step 1204 can calculate a CST for both the Gastrocnemius muscle and the Tibialis anterior muscle.

Once the CSTs 1002 are determined in the calculate neural drive step 1204, the neuromuscular assessment system 100 can execute a CST comparison step 1206. The CST comparison step 1206 can calculate the correlations for the CST 1002 of the Gastrocnemius muscle and the CST 1002 of the Tibialis anterior muscle. Alternatively, the CST comparison step 1206 can calculate the correlations for the motor unit spike trains 912 rather than the CSTs 1002.

Once the correlations for the CSTs 1002 are calculated, the neuromuscular assessment system 100 can execute a report step 1208. The report step 1208 can generate important pre-Parkinson's disease information of the CSTs 1002 and the motor unit spike trains 912. Illustratively, freeze of gait fraction 238 can be determined.

Figure 16A:
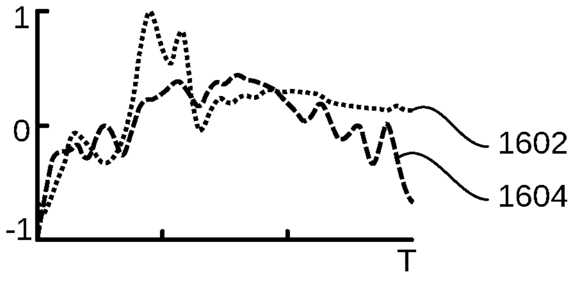
FIG. 16A is a graphical depiction of an EMG signal output channel from each of the combination sensors of FIG. 14 for a patient exhibiting a normal gait.
Figure 16B:
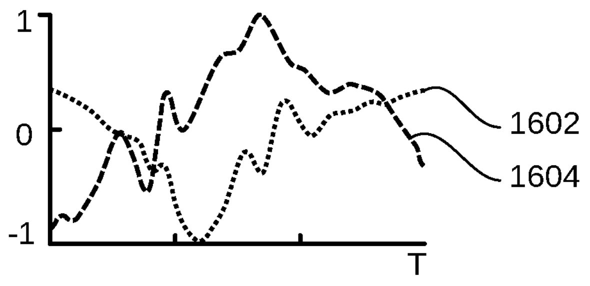
FIG. 16B is a graphical depiction of an EMG signal output channel from each of the combination sensors FIG. 14 for a patient exhibiting a shuffling freeze of gait.

As depicted in FIG. 16B, the freeze of gait can be identified by asynchrony between the agonist/antagonist muscle pair in the CSTs 1002 or the motor unit spike trains 912. The asynchrony can be illustratively determined with a cross-correlation between the CST 1002 of the Gastrocnemius muscle and the CST 1002 of the Tibialis anterior muscle.

The cross-correlation between the CST 1002 of the Gastrocnemius muscle and the CST 1002 of the Tibialis anterior muscle can be asynchronous if Parkinson's or pre-Parkinson's freeze of gait symptoms are present. Innervation patterns of the input CSTs 1002 can have an asynchronous correlation when the innervation of the agonist/antagonist muscles do not start or end at the same time, which is also described as a phase shift in the input CSTs, and which can be determined with an asynchronous gait threshold 1212.

That is, the cross-correlation of the CST 1002 of the Gastrocnemius muscle and the CST 1002 of the Tibialis anterior muscle can be comprised of a smaller peak next to a larger peak. This is indicative of asynchrony or a phase shift between the input CSTs 1002 of the cross-correlation.

The asynchronous gait threshold 1212 can be a measure of time or phase shift between the correlated signals. Illustratively, for example, when the correlated signals have a two peak periodic wave as is shown in FIG. 11K, the asynchronous gait threshold 1212 can be used to measure the distance between the smaller and larger peaks. If the distance in time between the peaks is larger than the asynchronous gait threshold 1212, then the correlated signals can be determined to be in asynchrony.

The freeze of gait fraction 238 can be the percentage of the correlated signals in asynchrony. Therefore, if three of four correlated signals show an asynchrony the freeze of gait fraction 238 would be 75%.

It is contemplated that the combination sensors 104 can be affixed to agonist/antagonist muscle pairs on multiple legs and the auto-correlations and cross-correlations could be computed for the HD-sEMG signals 208 from two pairs of the combination sensors 104 as is done in FIG. 11A through FIG. 11L. The freeze of gait fraction 238 over time can be reported as the Parkinson's progression score 234 of FIG. 2. Alternatively, the freeze of gait fraction 238 and the tremor fraction 236 of FIG. 2 can be averaged at each determination of the freeze of gait fraction 238 and the tremor fraction 236 and provided as the Parkinson's progression score 234.

Another aspect of the neuromuscular assessment system 100 can be a convolutional neural network 1220. The convolutional neural network 1220 can be a continuous learning algorithm having the individual motor unit spike trains 912 as inputs and the freeze of gait fraction 238 an output.

It is contemplated that the convolutional neural network 1220 can include hidden layers employing a sigmoid activation function, which provides results from 0 to 1 and is useful to predict probabilities such as the total tremor fraction 330. Furthermore, the hidden layers can employ a tanh activation function for hidden states.

Still further, the hidden layers can employ a softmax activation function, which is contemplated to determine the non-co-occurrence in the MUAPs 920 of FIG. 9. Yet still further, error can be computed using the mean absolute error activation function. The recurrent units occur in hidden layers.

Figure 13:
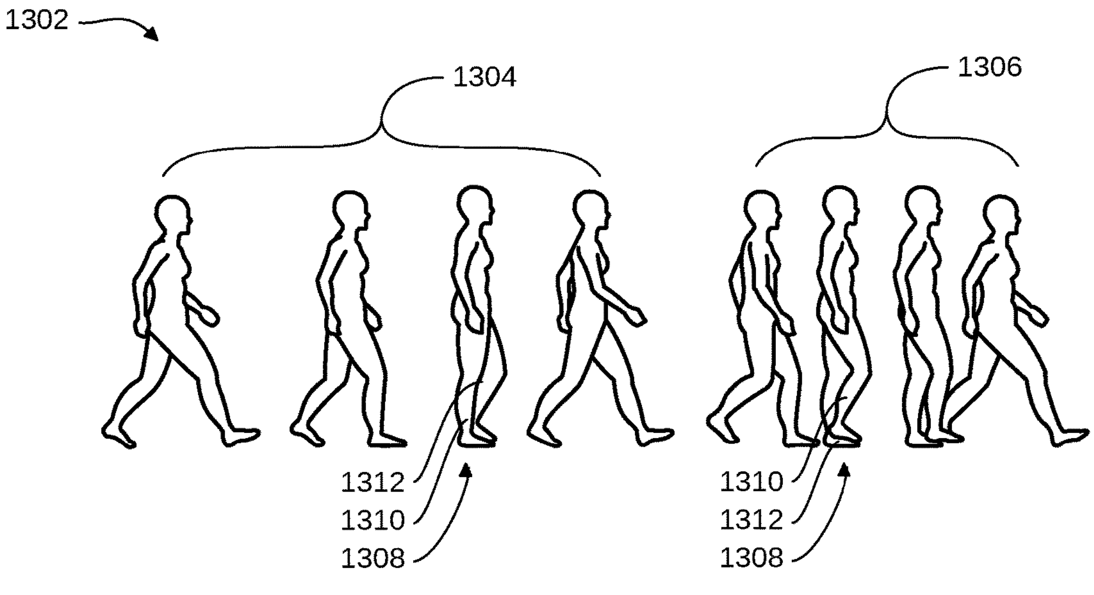
FIG. 13 is a side view depicting human gait of the patient.

Referring now to FIG. 13, therein is shown a side view depicting human gait 1302 of the patient 120. The patient 120 can be seen in both normal gait 1304 and freeze of gait 1306.

Of note, the patient 120 can be seen in a mid stance phase 1308 in both the normal gait 1304 and freeze of gait 1306. The mid stance phase 1308 in the normal gait 1304 is shown with the patient having a right leg 1310 on the ground and a left leg 1312 partially lifted.

The mid stance phase 1308 in the normal gait 1304 is followed by a heel off phase 1314 in which the left leg 1312 swings forward and the heel of the right leg 1310 comes off the ground. Conversely, the mid stance phase 1308 in the freeze of gait 1306 is followed by a freeze phase 1316.

The freeze phase 1316 can be a position where the leg stops forward motion. Following the freeze phase 1316, the freeze of gait 1306 will exhibit the heel off phase 1314.

In later stages of Parkinson's disease, the freeze of gait 1306 can be observed in the EMG readings or by visually observing the patient 120. However, early stage and pre-Parkinson's symptoms are not so easily identifiable and previous developments have failed to provide technical solutions to early detection. However, the technical solution of determining asynchrony as described in the calculate neural drive step 1204 of FIG. 12 and the CST comparison step 1206 of FIG. 12 enable and allow early stage generation of pre-Parkinson's disease information based on freeze of gait 1306.

Figure 14:
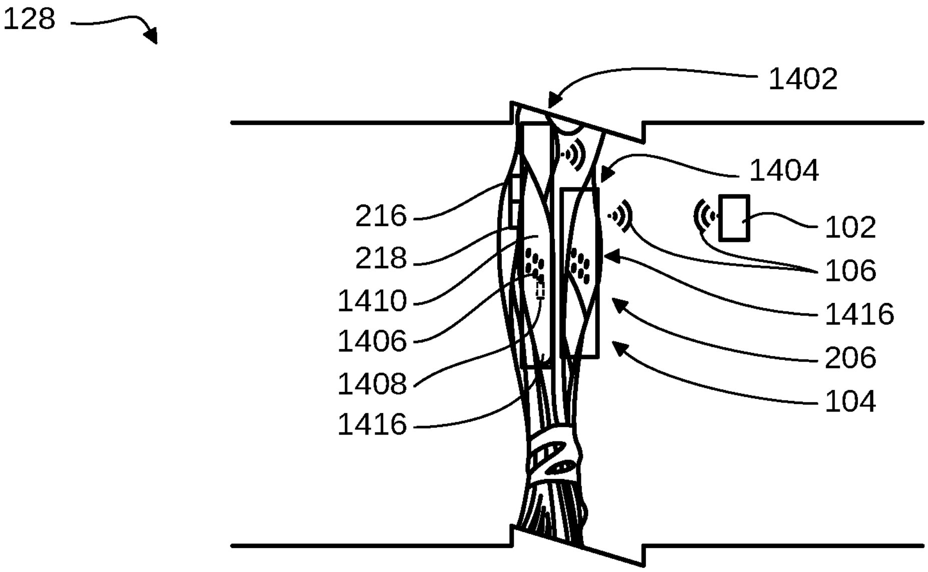
FIG. 14 is a side view of the lower leg of FIG. 1.

Referring now to FIG. 14, therein is shown a side view of the lower leg 128 of FIG. 1. The lower leg 128 is depicted as a right lower leg having the combination sensors 104 affixed thereto. For a depiction of the agonist/antagonist muscle pair discussed, skin is not shown and the underlying muscles are depicted; however, it is to be understood that the combination sensors 104 are affixed to or on the skin 412 of FIG. 4 of the patient 120 of FIG. 1 when in use. It is contemplated that any agonist/antagonist muscle pair in the leg or even in the foot could be used for the neuromuscular assessment system 100 of FIG. 1 by affixing the combination sensors 104 thereto.

Particularly, the combination sensors 104 can include a first combination sensor 1402 and a second combination sensor 1404. Each of the combination sensors 104 can include the HD-sEMG 206, the IMU 216, and the PPG sensor 218.

The HD-sEMG 206 can include multiple electrodes 1406 with a known and fixed distance 1408 between each of the electrodes 1406. The electrodes 1406 can be arranged in a grid configuration. Here, the electrodes 1406 are shown in a two by three grid configuration.

The electrodes 1406 can be set within an electrode carrier 1410. It is contemplated that the electrode carrier 1410 can be a Polyimide material roughly 50 μm thick.

It is further contemplated that the electrodes 1406 can be a silver or a silver chloride material providing an impedance between skin (not shown) and the electrode 1406 of about five Kilo-ohms. In a worst case scenario, the impedance could reach one Mega-ohm and maintain functionality.

The electrodes 1406 themselves are contemplated to have a small diameter of less than three to five millimeters. Furthermore, the fixed distance 1408 between the electrodes 1406 should be less than eight to ten millimeters.

It is contemplated that the combination sensors 104 can be placed on multiple different agonist/antagonist muscle pairs on the lower leg 128 when targeting the freeze of gait. Here, the first combination sensor 1402 is affixed to the skin (not shown) over a Tibialis anterior muscle 1414 while the second combination sensor 1404 is affixed to the skin (not shown) over a Gastrocnemius muscle 1416.

The wireless transmission 106 can communicate the combination sensor output signal 108 of FIG. 1 to the components box 102. It is alternatively contemplated that the components box 102 could be formed integrally with one or more of the combination sensors 104, which can reduce the amount of wiring needed.

Figure 15A:
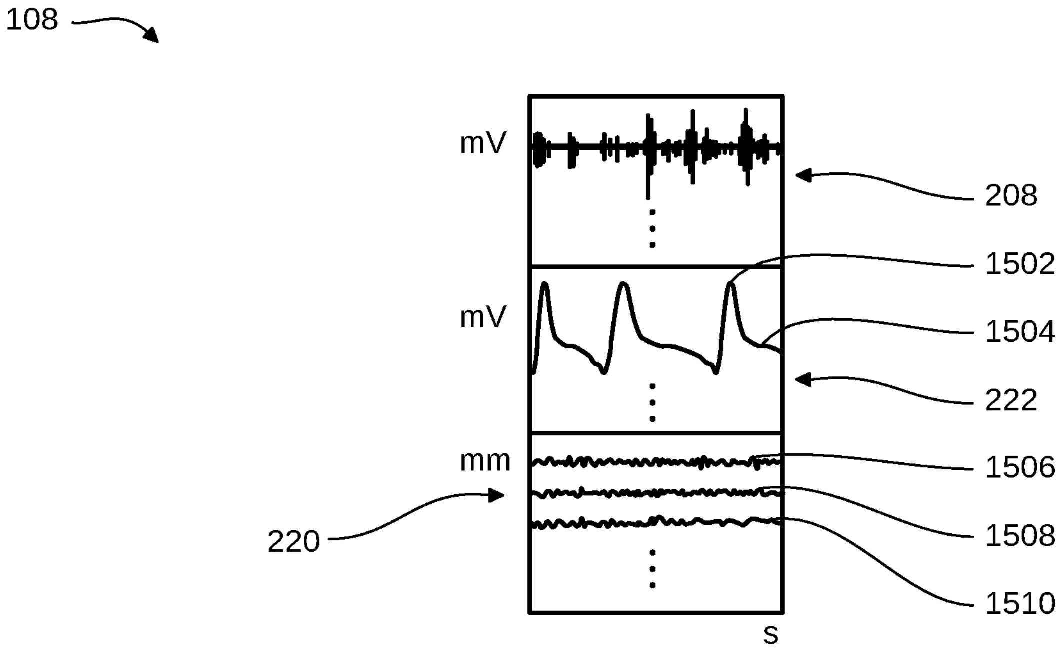
FIG. 15A is a graphical depiction of the combination sensor output signal of FIG. 1 for combination sensors of FIG. 1 while standing still.

The HD-sEMG 206 can provide multiple EMG channels of FIG. 15A, and also as depicted in FIG. 9A with each EMG signal channel generated by one of the electrodes 1406 closely spaced at the fixed distance 1408 on the skin of the patient 120. The multiple EMG channels contained within the HD-sEMG signal 208 can be analyzed within the processor 112 of FIG. 1 to generate the neural drive signal 210.

It has been discovered that utilizing the multiple electrodes 1406 arranged in a grid with the fixed distance 1408 enables the spatial dimension of the neural drive signal 210 to be identified for each of the MUAPs 920 of FIG. 9B. The discovery further enables the neural drive signal 210 to be evaluated for generating the pre-Parkinson's disease information before the symptoms become observable by a physician.

Figure 15B:
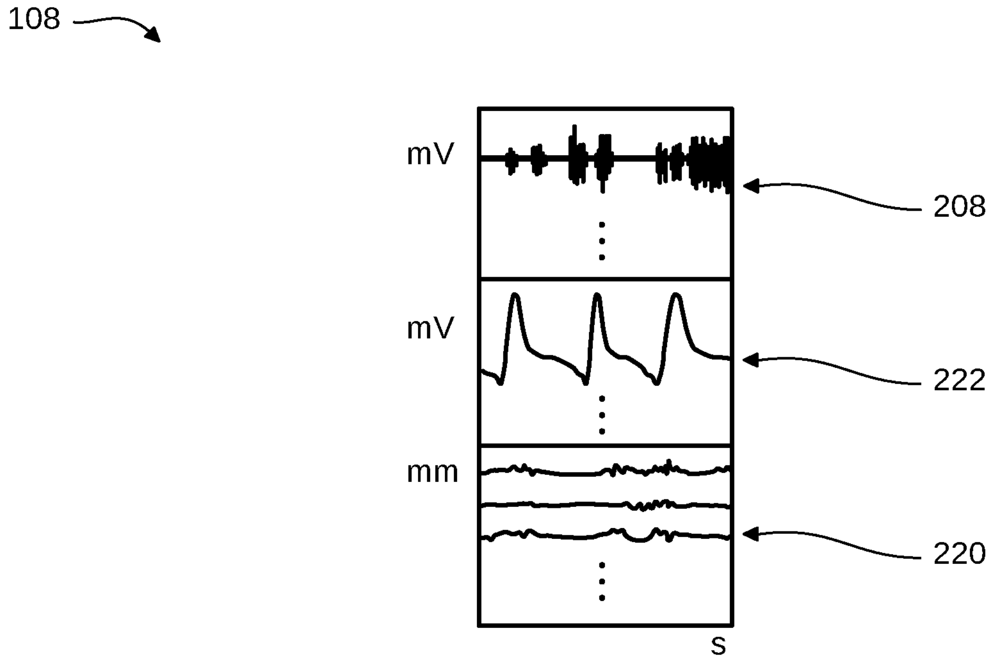
FIG. 15B is a graphical depiction of the combination sensor output signal of FIG. 1 for combination sensors of FIG. 1 while experiencing a freeze of gait.

Referring generally to FIG. 15A and FIG. 15B, the combination sensor output signal 108 of FIG. 1 is shown in each of the graphical depictions, which serve to illustrate the HD-sEMG signals 208, the IMU signals 220, and the PPG signals 222, each of FIG. 2. Importantly, the IMU signal 220 shows no difference between standing still and a freeze of gait. That is, the accelerometers within the IMU 216 of FIG. 2 do not distinguish between the standing still shown in 15A and the freeze of gait shown in FIG. 15B.

This is evident between the combination sensor output signal 108 depicted in FIG. 15A and FIG. 15B showing little distinguishing factors between them. It will be understood however, that the HD-sEMG signals 208 can be decomposed into the motor unit spike trains 912 and further summed to provide the CST 1002 of FIG. 10, which is the neural drive signal 210 for a muscle and can be correlated as shown in FIG. 11A through FIG. 11L and generate pre-Parkinson's disease information based on divergence between the agonist/antagonist muscle pair indicating freeze of gait at the neural drive level which is indicative of Parkinson's disease.

Referring now to FIG. 15A, therein is shown a graphical depiction of the combination sensor output signal 108 of FIG. 1 for combination sensors 104 of FIG. 1 while standing still. The HD-sEMG signal 208 can include an HD-sEMG signal for the electrode array of the combination sensors 104 for the Gastrocnemius muscle 1416 of FIG. 14 and the Tibialis anterior muscle 1414 of FIG. 14.

For descriptive clarity, the full set of the HD-sEMG signals 208 for the entire array of the combination sensors 104 is not shown. Ellipses are used to depict the rest of the EMG signals from the other electrodes 1406 on either the Gastrocnemius muscle 1416 or the Tibialis anterior muscle 1414. The vertical axis for the HD-sEMG signal 208 can be a measurement of millivolts while the horizontal axis can be a measurement of time in seconds or milliseconds.

Freeze of gait can involve agonist/antagonist muscle pair mis-matches during a gait cycle. This is shown for example in FIG. 16B with the Tibialis anterior muscle exhibiting repeated contraction and stretching, while the Gastrocnemius muscle remains essentially stretched.

The pre-Parkinson's disease information can be generated based on agonist/antagonist muscle pair mis-matches during a gait cycle, which is detectable early when the neural drive is evaluated. The neural drive is evaluated when the motor unit spike trains 912 of FIG. 9 are decomposed from the HD-sEMG signal 208 from multiple electrodes 1406 of FIG. 14.

Evaluating the motor unit spike trains 912 from multiple electrodes 1406 allows a spatial triangulation of muscle activity and activation over time and provides a technical solution and advantage over previous methods that did not utilize the disclosed decomposition, cross-correlation evaluation of the neural drive, or the array of electrodes to provide the HD-sEMG signal 208.

In later stages of Parkinson's disease, the agonist/antagonist asynchrony can be observed in the EMG readings or by visually observing the patient 120 of FIG. 1. However, early stage and pre-Parkinson's disease information is not so easy to generate but can be accomplished with the methods proposed herein.

That is, the array of the electrodes 1406 can provide a spatial dimension to the data allowing neural drive signals 210 of FIG. 2 to be identified and compared to generate pre-Parkinson's disease information, which is not obtainable by previous developments in the art.

The combination sensor output signal 108 can further include the PPG signals 222 of the combination sensors 104. The waveform of the PPG signals 222 is produced by variations in the attenuation of a light energy as it passes through, is scattered and reflected within, or is absorbed by biological tissues prior to being detected with an optical sensor.

For descriptive clarity only a single PPG signal 222 is shown for the combination sensors 104 and ellipses are used to depict the other PPG signal 222 from the pair of combination sensors 104, one coupled to the Gastrocnemius muscle 1416 and the other coupled to the Tibialis anterior muscle 1414.

The vertical axis can be a measurement of volts in millivolts, while the horizontal axis can be a measurement of time in seconds or milliseconds. Analysis of the PPG signal 222 within the signals block 204 of FIG. 2 can provide an indication of the blood pressure 224 of FIG. 2 with an estimation of a systole pulse wave 1502 and diastole pulse wave 1504. Further, a time interval between systole pulse waves can be determined, from which the heart rate 225 of FIG. 2 and the heart rate variability 226 of FIG. 2 can be derived.

For example, the heart rate 225 can be sixty divided by the time in seconds between systole pulse waves 1502. The heart rate variability 226 can be computed from the heart rate 225 or directly from the systole pulse waves 1502. The heart rate variability 226 is an early indicator of Parkinson's disease but is not adequately specific by itself. It is contemplated therefore to combine the heart rate variability 226 with the HD-sEMG signals 208 to advance specificity.

The combination sensor output signal 108 is further shown with the IMU signals 220 of the combination sensors 104. The IMU signals 220 can include an x-plane acceleration 1506, a y-plane acceleration 1508, and a z-plane acceleration 1510. The x-plane acceleration 1506, the y-plane acceleration 1508, and the z-plane acceleration 1510 correspond to one of the combination sensors 104 coupled to the lower leg 128 of FIG. 1 as depicted by FIG. 14.

For descriptive clarity only a single IMU signal 220 is shown for the lower leg 128 and ellipses are used to depict the other IMU signal 220 from the pair of combination sensors 104, one coupled to the Gastrocnemius muscle 1416 and the other coupled to the Tibialis anterior muscle 1414. The vertical axis can be a measurement of physical displacement in millimeters and the horizontal axis can be a measurement of time in milliseconds.

Referring now to FIG. 15B, therein is shown a graphical depiction of the combination sensor output signal 108 of FIG. 1 for combination sensors 104 of FIG. 1 while experiencing a freeze of gait. FIG. 15B depicts the combination sensor output signal 108 in a similar fashion as FIG. 15A. The combination sensor output signal 108 is shown having the HD-sEMG signal 208, the IMU signal 220, and the PPG signal 222.

Prior to extracting the neural drive by decomposition of the HD-sEMG signals 208 into the motor unit spike trains 912 of FIG. 9, freeze of gait 1306 of FIG. 13 is difficult to determine and prior developments lacked the technical ability to generate pre-Parkinson's disease information between freeze of gait and standing still from the IMU 216 of FIG. 2 alone. This is evident between the combination sensor output signal 108 depicted in FIG. 15A and FIG. 15B showing little distinguishing factors between them.

Decomposing the HD-sEMG signal 208 into the motor unit spike trains 912 and summing them to provide the CST 1002 of FIG. 10, enable the CSTs 1002 for the agonist/antagonist muscle pair, such as the Gastrocnemius muscle and the Tibialis anterior muscle, to be cross-correlated. This cross-correlation of the CSTs 1002 can provide a measure of difference between the neural drive of the two muscles which directly relates to the progression of Parkinson's disease.

Referring generally to FIG. 16A and FIG. 16B, the regular gait shown in FIG. 16A illustrates the largely synchronous firing of the agonist/antagonist muscles while the shuffling freeze of gait shown in FIG. 16B illustrates the signals diverging asynchronously. While this can be seen in the HD-sEMG signal 208, the measure of degree of divergence must be accomplished at the neural drive level; which can include the decomposition of the HD-sEMG signal 208 into the motor unit spike trains 912 of FIG. 9, the summation of the motor unit spike trains 912 into the CST 1002 of FIG. 10, and the cross-correlation of the CSTs 1002 of the agonist/antagonist muscle pair.

Referring now to FIG. 16A, therein is shown a graphical depiction of an EMG signal output channel from each of the combination sensors 104 of FIG. 14 for a patient exhibiting a normal gait. Illustratively, a first EMG channel 1602 can be provided from the combination sensor 104 attached to the Tibialis anterior muscle 1414 of FIG. 14 while a second EMG channel 1604 can be provided from the combination sensor 104 attached to the Gastrocnemius muscle 1416 of FIG. 14.

The first EMG channel 1602 and the second EMG channel 1604 are shown with a vertical axis providing a normalized amplitude from negative one to positive one, while the horizontal axis provides time in one second divisions. The first EMG channel 1602 and the second EMG channel 1604 are largely synchronous in their firing.

Referring now to FIG. 16B, therein is shown a graphical depiction of one EMG signal output channel from each of the combination sensors 104 of FIG. 14 for a patient exhibiting a shuffling freeze of gait. Similar to FIG. 16A above, the first EMG channel 1602 can be provided from the combination sensor 104 attached to the Tibialis anterior muscle 1414 of FIG. 14 while the second EMG channel 1604 can be provided from the combination sensor 104 attached to the Gastrocnemius muscle 1416 of FIG. 14.

The first EMG channel 1602 and the second EMG channel 1604 are shown with a vertical axis providing a normalized amplitude from negative one to positive one, while the horizontal axis provides time in one second divisions. The first EMG channel 1602 and the second EMG channel 1604 diverge remarkably during the freeze of gait.

The divergence between the first EMG channel 1602 and the second EMG channel 1604 will drift away from each other over time when freeze of gait is present. This drifting can be tracked using convolution outputs as described with regard to the convolutional neural network 1220 FIG. 12. Otherwise, the CST 1002 of FIG. 10 for the Gastrocnemius muscle 1416 and the CST 1002 for the Tibialis anterior muscle 1414 can be cross-correlated to determine how much the Gastrocnemius muscle 1416 and the Tibialis anterior muscle 1414 diverge or are asynchronous at the neural drive level, which directly relates to Parkinson's disease progression.

Figure 17A:
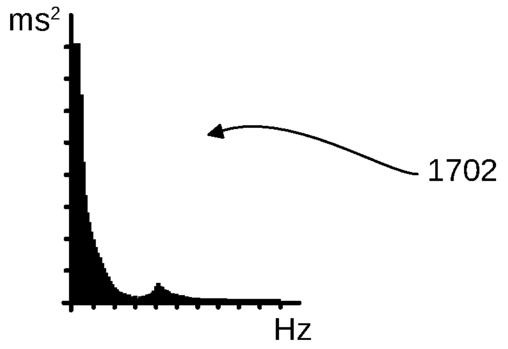
FIG. 17A is a graphical depiction of a power spectral density estimate for a heart rate variability of a healthy patient.

Referring now to FIG. 17A, therein is shown a graphical depiction of a power spectral density estimate for a heart rate variability of a healthy patient. Heart rate and heart rate variability (HRV) are not specific to Parkinson's but could be due to many issues including heart deficiencies, lung deficiencies, and even mental depressions.

However, HRV is present in Parkinson's patients, and combining an indication of HRV determined by the PPG sensor 218 of FIG. 2 with the neural drive signal 210 of FIG. 2 can provide a more powerful and specific tool for the indication of Parkinson's disease and Parkinson's disease progression.

The PPG signal 222 of FIG. 2 can be processed within the processor 112 of FIG. 1 to provide the power spectral density estimate. Illustratively, the power spectral density estimate can be a frequency domain graph with the vertical axis expressed in absolute power which is milliseconds squared divided by cycles per second in 10,000 per division. The horizontal axis can provide frequency in 0.05 hertz per division.

The power spectral density estimate can be determined by the processor 112 with a nonparametric method or a parametric method. Illustratively, the fast Fourier transformation is an example of the nonparametric method while an autoregressive model estimation is an example of a parametric method.

The power spectral density estimate for the healthy patient is shown having an RR interval (RRI) of 876 milliseconds, and a Standard Deviation of normal to normal R-R Intervals (SDNN) of 131 milliseconds. The SDNN can denote the median of the variability of heart rate.

The power spectral density estimate can depict a VLF range between 0.0033-0.04 hertz, which is comprised of rhythms with periods between 25 and 300 seconds. The VLF range can have a power of 2827 milliseconds squared over cycles per second.

The power spectral density estimate can depict a LF range between 0.04-0.15 hertz, which is comprised of rhythms with periods between 7 and 25 seconds. The LF range can have a power of 891 milliseconds squared over cycles per second.

The power spectral density estimate can depict a HF range between 0.15-0.40 hertz. The HF range can have a power of 423 milliseconds squared over cycles per second.

Figure 17B:
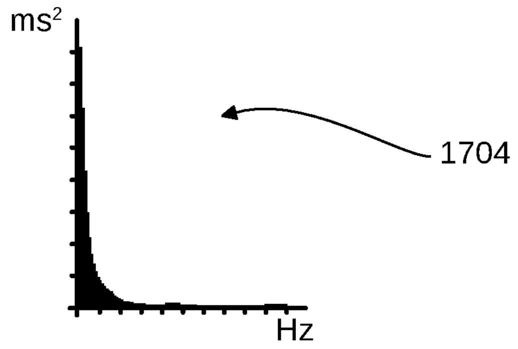
FIG. 17B is a graphical depiction of a power spectral density estimate for a heart rate variability of a Parkinsonian patient.

Referring now to FIG. 17B, therein is shown a graphical depiction of a power spectral density estimate for a heart rate variability of a Parkinsonian patient. The PPG signal 222 of FIG. 2 can be processed within the processor 112 of FIG. 1 to provide the power spectral density estimate. Illustratively, the power spectral density estimate can be a frequency domain graph with the vertical axis expressed in absolute power which is milliseconds squared divided by cycles per second in 10,000 per division. The horizontal axis can provide frequency in 0.05 hertz per division.

The power spectral density estimate for the Parkinson's patient is shown having an RRI of 822 milliseconds, and a SDNN of 93 milliseconds. The power spectral density estimate can depict a VLF range with a power of 1225 milliseconds squared over cycles per second, an LF with a power of 362 milliseconds squared over cycles per second, and a HF range with a power of 102 milliseconds squared over cycles per second.

The power of each frequency range is much lower with the Parkinson's patient of FIG. 17B than the healthy patient of FIG. 17A. Illustratively, for example when the Parkinson's readings are compared with the healthy patient readings, the VLF falls to less than half, the LF falls to less than half, and the HF falls to less than a quarter.

When HRV 226 of FIG. 2 is detected above the HRV threshold 227, a HRV bonus can be added to the Parkinson's propensity score 232, the tremor fraction 236, the freeze of gait fraction 238, and the Parkinson's progression score 234, all of FIG. 2. The HRV bonus could for example be an increase in ten percentage points if the HRV 226 is detected above the HRV threshold 227.

Similarly, initial orthostatic hypotension (IOH), which occurs during the initial thirty seconds after standing can be detectable with the sophisticated and continuous monitoring of the combination sensors 104 containing the PPG sensor 218 and providing the PPG signal 222. When for example, the systole pulse wave 822 of FIG. 8 representing blood pressure 224 of FIG. 2 drops below the IOH threshold 228, an IOH bonus can be added to the Parkinson's propensity score 232, the tremor fraction 236, the freeze of gait fraction 238, and the Parkinson's progression score 234.

The IOH bonus could, for example, be an increase in ten percentage points if the systole pulse wave 822, representing blood pressure 224, drops below the IOH threshold 228. These cardiovascular parameters among others, have a relationship to Parkinson's disease and can be used to modify pre-Parkinson's disease information, which can enable even earlier and robust diagnoses.

Figure 18:
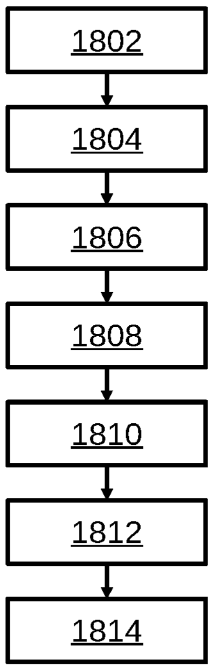
FIG. 18 is a control flow of a method for operating the neuromuscular assessment system 100.

Referring now to FIG. 18, therein is shown a control flow of a method for operating the neuromuscular assessment system 100. The control flow can include: affixing a first electrode in a first electrode array to an agonist muscle configured to detect a first Electromyography (EMG) signal in a block 1802; affixing a second electrode in a second electrode array to an antagonist muscle configured to detect a second EMG signal, the agonist muscle and the antagonist muscle forming an agonist/antagonist muscle pair in a block 1804; decomposing the first EMG signal into a first motor unit spike train in a block 1806; decomposing the second EMG signal into a second motor unit spike train in a block 1808; correlating the first motor unit spike train and the second motor unit spike train to generate a correlated signal in a block 1810; determining synchronicity and periodicity within the correlated signal in a block 1812; and generating pre-Parkinson's disease information including a tremor fraction, the tremor fraction being a fraction of the correlated signals determined to have both the synchronicity and the periodicity in a block 1814.

Thus, it has been discovered that the neuromuscular assessment system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the neuromuscular assessment system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. A method of operating a neuromuscular assessment system comprising:

affixing a first electrode array to an agonist muscle, the first electrode array configured to detect a first Electromyography (EMG) signal comprising a first plurality of EMG channels;

affixing a second electrode array to an antagonist muscle, the second electrode array configured to detect a second EMG signal comprising a second plurality of EMG channels, the agonist muscle and the antagonist muscle forming an agonist/antagonist muscle pair;

determining a spatial triangulation of muscle activity and motor unit activation over time by analyzing, via a processor, the first plurality of EMG channels and the second plurality of EMG channels of the first EMG signal and the second EMG signal, respectively, wherein the analyzing comprises decomposing the first EMG signal and the second EMG signal into a first plurality of motor unit spike trains and a second plurality of motor unit spike trains, respectively;

summing the first plurality of motor unit spike trains and the second plurality of motor unit spike trains into a first cumulative spike train and a second cumulative spike train, respectively:

generating, based on cross-correlations of the first cumulative spike train and the second cumulative spike train, correlated signals representing a cross-correlation between the agonist and antagonist muscles of the muscle pair;

determining synchronicity and periodicity within the correlated signals, wherein the periodicity is determined by calculating a power spectral density of the correlated signals; and generating a tremor fraction, the tremor fraction being a percentage of the correlated signals determined to have both the synchronicity and the periodicity, and the tremor fraction indicative of a resting tremor before the resting tremor is physically observable.

2. The method of claim 1 further comprising:

determining asynchrony within the correlated signals;

generating a freeze of gait fraction, the freeze of gait fraction being a second percentage of the correlated signals determined to have the asynchrony; and wherein:

affixing the first electrode array and affixing the second electrode array include affixing the first electrode array and the second electrode array to the agonist/antagonist muscle pair within a leg.

3. The method of claim 1 further comprising:

low pass filtering the first motor unit spike train and the second motor unit spike train.

4. The method of claim 1 wherein:

determining the synchronicity includes determining one of the correlated signals include peaks separated by a time, the time being below a synchronicity threshold.

5. The method of claim 1 further comprising:

affixing a Photoplethysmography sensor configured to detect a cardiovascular parameter; and increasing the tremor fraction based on the cardiovascular parameter.

6. The method of claim 1 further comprising:

affixing a first inertial measurement unit (IMU) and a second IMU, the first IMU and the second IMU configured to generate IMU signals; and increasing the tremor fraction based on the IMU signals being bilaterally asymmetric.

7. A non-transitory computer readable medium in useful association with a processor having instructions configured to:

generate a first Electromyography (EMG) signal comprising a first plurality of EMG channels from a first electrode array affixed to an agonist muscle;

generate a second EMG signal comprising a second plurality of EMG channels from a second electrode array affixed to an antagonist muscle, the agonist muscle and the antagonist muscle forming an agonist/antagonist muscle pair;

determine a spatial triangulation of muscle activity and motor unit activation over time by analyzing, via the processor, the first plurality of EMG channels and the second plurality of EMG channels of the first EMG signal and the second EMG signal, respectively, wherein the analyzing comprises decomposing the first EMG signal and the second EMG signal into a first plurality of motor unit spike trains and a second plurality of motor unit spike trains, respectively;

sum the first plurality of motor unit spike trains and the second plurality of motor unit spike trains into a first cumulative spike train and a second cumulative spike train, respectively;

generate, based on cross-correlations of the first cumulative spike train and the second cumulative spike train, correlated signals representing a cross-correlation between the agonist and antagonist muscles of the muscle pair;

determine synchronicity and periodicity within the correlated signals, wherein the periodicity is determined by calculating a power spectral density of the correlated signals; and generate a tremor fraction, the tremor fraction being a percentage of the correlated signals determined to have both the synchronicity and the periodicity, and the tremor fraction indicative of a resting tremor before the resting tremor is physically observable.

8. The computer readable medium of claim 7 further comprising:

instructions configured to determine asynchrony within the correlated signals from the agonist/antagonist muscle pair within a leg; and instructions configured to generate a freeze of gait fraction, the freeze of gait fraction being a second percentage of the correlated signals determined to have the asynchrony.

9. The computer readable medium of claim 8 further comprising:

instructions configured to generate IMU signals from a first inertial IMU and a second IMU; and instructions configured to increase the tremor fraction based on the IMU signals being bilaterally asymmetric.

10. The computer readable medium of claim 7 further comprising: instructions configured to low pass filter the first motor unit spike train and the second motor unit spike train.

11. The computer readable medium of claim 7 wherein: the instructions configured to determine the synchronicity include instructions configured to determine one of the correlated signals include peaks separated by a time, the time being below a synchronicity threshold.

12. The computer readable medium of claim 7 further comprising:

instructions configured to generate a cardiovascular parameter based on a Photoplethysmography sensor; and instructions configured to increase the tremor fraction based on the cardiovascular parameter.

13. A neuromuscular assessment system comprising:

a first electrode array configured for attachment to an agonist muscle and configured to detect a first Electromyography (EMG) signal comprising a first plurality of EMG channels;

a second electrode array configured for attachment to an antagonist muscle and configured to detect a second EMG signal a second plurality of EMG channels, the agonist muscle and the antagonist muscle forming an agonist/antagonist muscle pair; and a processor configured to:

determine a spatial triangulation of muscle activity and motor unit activation over time by analyzing, via the processor, the first plurality of EMG channels and the second plurality of EMG channels of the first EMG signal and the second EMG signal, respectively, wherein the analyzing comprises decomposing the first EMG signal and the second EMG signal into a first plurality of motor unit spike trains and a second plurality of motor unit spike trains, respectively;

sum the first plurality of motor unit spike trains and the second plurality of motor unit spike trains into a first cumulative spike train and a second cumulative spike train, respectively;

generate, based on cross-correlations of the first cumulative spike train and the second cumulative spike train, correlated signals representing a cross-correlation between the agonist and antagonist muscles of the muscle pair;

determine synchronicity and periodicity within the correlated signals, wherein the periodicity is determined by calculating a power spectral density of the correlated signals; and generate a tremor fraction, the tremor fraction being a percentage of the correlated signals determined to have both the synchronicity and the periodicity, and the tremor fraction indicative of a resting tremor before the resting tremor is physically observable.

14. The system of claim 13 wherein:

the processor is configured to determine asynchrony within the correlated signals and generate a freeze of gait fraction, the freeze of gait fraction being a second percentage of the correlated signals determined to have the asynchrony; and the agonist/antagonist muscle pair is within a leg.

15. The system of claim 13 wherein: the processor is configured to low pass filter the first motor unit spike train and the second motor unit spike train.

16. The system of claim 13 wherein:

the processor is configured to determine one of the correlated signals include peaks separated by a time, the time being below a synchronicity threshold.

17. The system of claim 13 further comprising:

a Photoplethysmography sensor configured to detect a cardiovascular parameter; and wherein:

the processor is configured to increase the tremor fraction based on the cardiovascular parameter.

18. The system of claim 13 further comprising:

a first IMU and a second IMU configured to generate IMU signals; and wherein:

the processor is configured to increase the tremor fraction based on the IMU signals being bilaterally asymmetric.

19. The method of claim 1, wherein the tremor fraction is generated via a neural network of the neuromuscular assessment system, the neural network configured to:

receive, as inputs, the first plurality of motor unit spike trains and the second plurality of motor unit spike trains;

generate, as output, the tremor fraction.

20. The method of claim 1, further comprising outputting a Parkinson's propensity score based on the tremor fraction, including at least one of outputting on a display or print out, through an audio device or speaker, or through a tactile or haptic device.

21. The method of claim 1, wherein each of the first EMG signal and the second EMG signal comprises a respective High Density-surface EMG signal.

* * * * *